United States Patent [19]

Nelson

[11] Patent Number: 5,156,975

[45] Date of Patent: Oct. 20, 1992

[54] FIELD DISPERSANT TEST FOR DETERMINING THE FOULING TENDENCY OF A CRUDE OIL PROCESS

[75] Inventor: Mark A. Nelson, Katy, Tex.

[73] Assignee: Nalco Chemical Company, Naperville, Ill.

[21] Appl. No.: 530,914

[22] Filed: Jul. 3, 1990

[51] Int. Cl.$^5$ .............................................. C10C 1/20
[52] U.S. Cl. ........................................ 436/140; 436/2; 436/60; 436/139; 436/164; 585/13; 585/950; 208/48 AA
[58] Field of Search ............... 436/55, 60, 2, 140, 436/141, 161, 162, 139, 164; 73/61.1, 61.2, 64; 585/1, 13, 950; 208/48 AA; 422/69, 68, 70; 210/658, 198.3

[56] References Cited

U.S. PATENT DOCUMENTS

| | | | |
|---|---|---|---|
| 4,762,797 | 8/1988 | Dickakian | 436/60 |
| 4,781,892 | 11/1988 | Dickakian | 422/69 |
| 4,781,893 | 11/1988 | Dickakian | 422/69 |
| 4,843,247 | 6/1989 | Yamazoe et al. | 250/523 |

OTHER PUBLICATIONS

Fields, D. E. et al., "Predicting Crude Oil Fouling Tendency", AICHE National Meeting Presentation, Mar. 10, 1988.

*Primary Examiner*—James C. Housel
*Assistant Examiner*—Lien T. Tran
*Attorney, Agent, or Firm*—Arnold, White & Durkee

[57] ABSTRACT

The methods and test kit of the present invention provide a fast, inexpensive, reproducible, simple, and accurate method for optimizing the dosage of an asphaltene dispersant antifouling agent for a given crude oil containing asphaltenes. A method is provided wherein a sample of the crude oil is diluted with a quantity of an aromatic organic solvent. To the diluted crude oil is added a known amount of the antifouling agent being evaluated. A portion of the diluted crude oil containing the antifouling agent is removed and mixed with a quantity of a liquid paraffinic hydrocarbon. The concentration of materials which remain dispersed in the liquid paraffinic hydrocarbon is measured. The inventive methods are useful to evaluate a single dose of an antifouling agent or may be used to simultaneously evaluate a plurality of doses in order to determine which dose is most effective for a given sample of crude oil.

16 Claims, 21 Drawing Sheets

FIELD DISPERSANT TEST FOR DETERMINING THE FOULING TENDENCY OF A CRUDE OIL PROCESS

BACKGROUND OF THE INVENTION

1. Field of the Invention

The present invention relates to a method and test kit for determining the tendency of a crude oil to foul oil field refinery equipment, and more particularly, to a method and test kit for optimizing the dosage of antifouling additives used in treating a given sample of crude oil.

2. Description of the Prior Art

Fouling is a common problem in the refining of crude oil. Fouling is defined for purposes of the present invention as the deposition of inorganic and carbonaceous substances on heated oil refinery surfaces by crude oil. These deposits reduce the rate of heat transfer to the crude oil, and eventually, reduce throughput rates. In fact, these deposits can, in some instances, block the flow of crude oil through the equipment. Fouling results in increased energy costs, increased maintenance costs, and capital expenditures for the modification or replacement of refinery equipment, e.g., heat exchangers.

The mechanism of fouling is not fully known. However, some investigators have suggested that several different components of crude oil may contribute to fouling; i.e., asphaltenes, coke, organic polymers and organic reaction products, inorganic silicates, inorganic salts, metal oxides or sulfides. Because fouling severely reduces efficiency in the refining of crude oil, there are a number of methods and devices which are designed to predict the fouling tendency of a particular crude oil.

One method which predicts the fouling tendency of a crude oil measures the rate of heat transfer from a heated refinery surface to the crude oil. The rate of heat transfer is inversely proportional to the deposition of fouling materials onto the heated refinery surface. For example, the crude oil temperature at the exit of a heat-exchanger is measured while the metal temperature of the heat-exchanger is controlled. As the fouling progresses, deposits build up on the heated surfaces of the heat exchanger. Significant fouling is indicated by a reduction of heat transfer, i.e., a decrease in the crude oil outlet temperature. The change in crude oil outlet temperature with time provides the basic heat data required for the comparative evaluation of different crude oils. This data is used to extrapolate the relative fouling tendency of a given crude oil.

This method is used in the laboratory in accelerated tests which are designed to reproduce the fouling problem experienced in a refinery over several months. Fouling acceleration is provided by carrying out tests at operating temperatures higher than those in operating refinery units. With the rate of fouling increased, a crude oil's fouling characteristics can be assessed in a shortened period of time, i.e., from about 3 to about 4 hours. Each test unit is capable of performing about 200 tests annually.

The above method is useful to determine the general propensity of a crude oil to foul equipment. Recently, however, one component of crude oil, asphaltenes, has been scrutinized as contributing heavily to the fouling problem. Therefore, methods and devices have been developed to help determine fouling profiles of crude oils containing asphaltenes. For example, U.S. Pat. Nos. 4,781,893, and 4,781,892 Dickakian, describe an apparatus and method for detecting the presence of incompatible asphaltenes in a given crude oil sample, and estimating the tendency of the crude oil to foul equipment. According to the patents, incompatible asphaltenes foul equipment by separating from the crude oil and adhering to a heated metal surface where they are changed into coke-like material. It is this coke-like material which fouls the heated surface. According to the method described in the referenced patents, a single drop of crude oil is deposited on a polymeric membrane constructed from polymers containing polar atoms. The sample migrates on the membrane to form concentric rings. The concentric rings consist of hydrocarbons separated by size and incompatible asphaltenes. Light reflected from the surface of the sample is processed to determine the constituents of each concentric ring. In this way the presence of incompatible asphaltenes is determined and the fouling tendency of oil is estimated.

Once the fouling tendency of a crude oil is estimated, the dosage of the antifouling agent is estimated. Antifouling agents are added to the crude oil during the refining process. Antifouling agents are utilized to help alleviate the problem of fouling. If the crude oil contains asphaltenes, asphaltene dispersants are typically added to the crude oil. These asphaltene dispersants suspend or disperse the agglomerated or precipitated asphaltenes in the crude oil. Therefore, asphaltenes do not precipitate from the crude oil onto the heated metal refinery surfaces where they foul the equipment.

Presently, the dosage of antifouling agent added to the crude oil is estimated by first estimating the fouling propensity of the crude oil. The greater the likelihood that the crude oil will foul equipment, the larger the dose of the antifouling agent added. However, estimating the dose of the antifouling agent is an inefficient and commercially unacceptable method for controlling the refining of crude oil.

The problem with estimating dosages is that if the dosage of the antifouling agent added to the crude oil is too low, throughput rates are lowered and equipment is damaged. Further, if the estimated dosage is too high, antifoulant is wasted, and accordingly, money is spent ineffectively. It becomes apparent when considering the world-wide need for oil and the limited resources available to develop it, that any vehicle which creates efficiencies in the refining of oil is potentially important commercially and socially. Accordingly, the refining industry requires more effective dosage control of the various chemical additives in their refineries. The purpose of dosage control devices or systems is to optimize on a more frequent basis the dosage required for a given refining process. In the past, as discussed above, optimization programs have proven to be minimal.

Although there are methods and devices available for estimating the fouling tendency of a crude oil containing asphaltenes, the results yielded are not specific enough to enable a unit operator to accurately and efficiently control asphaltene fouling during the refining process. Further, these estimation methods are time consuming and expensive. For example, estimating the fouling tendency of a crude oil based on the rate of heat exchanged over a period of time is an expensive and time consuming process. This procedure requires a specially constructed heat-exchanging unit which must be operated in a laboratory. The process requires three to four hours to complete for each sample, and the units must be thoroughly cleaned between trials. Furthermore, each unit typically only evaluates about 200 samples annually. Thus, in order to complete a comparative evaluation study of antifoulant treated crude oil and untreated crude oil, several days, if not weeks, would be required. This reduces the applicability of the process to long-term planning, and accordingly, the process is relatively useless in the short-term efficient refining of crude oil.

The methods and devices described in the 4,781,893 and 4,781,892 patents require from several minutes to several hours for the development of the measurable chromatographic pattern. These methods are directed to determining the relative presence of asphaltenes in a crude oil. From this data the relative fouling tendency of a given crude oil sample is estimated. These methods and apparatus are not directed to optimizing the dosage of a particular antifouling agent in a given crude oil sample. In fact, these references even fail to identify the accurate dosing of antifouling agents as critical to the efficient refining of crude oil. Thus, these methods are not applicable to the on-site "fine tuning" of the refining process.

Hence, in light of the deficiencies in the art set forth above, it would be advantageous to provide a fast, accurate, simple, reproducible, and inexpensive method for optimizing the dosage of an antifouling agent necessary to add to a given sample of crude oil to alleviate asphaltene fouling of oil refinery equipment. Further, it would be even more advantageous to provide a method which could be employed on-site in the refinery by unit operators without extensive chemical training to optimize the dosage of a particular antifouling agent that when added to the crude oil would alleviate asphaltene equipment fouling. Therefore, it would be particularly advantageous to provide a test kit for use by unit operators which would not only monitor the asphaltene fouling tendency of a crude oil but would also optimize the dose of an antifouling agent necessary to add to a crude oil to alleviate asphaltene fouling.

SUMMARY OF THE INVENTION

The present invention is directed to providing a method and test kit for optimizing the dosage of an asphaltene dispersant antifouling agent for a given crude oil containing asphaltenes.

One aspect of the present invention achieves these results by providing a method for evaluating the antifouling effectiveness of a dose of an asphaltene dispersant antifouling agents. A sample of the crude oil is diluted with a quantity of an aromatic organic solvent. To the diluted crude oil is added a known amount of the antifouling agent being evaluated. A portion of the diluted crude oil containing the antifouling agent is removed and mixed with a quantity of a liquid paraffinic hydrocarbon. The concentration of materials which remain dispersed in the liquid paraffinic hydrocarbon is thereafter measured.

Another aspect of the present invention achieves the above results by providing a process for optimizing the dosage of an asphaltene dispersant antifouling agent in a crude oil containing asphaltenes by simultaneously evaluating a plurality of doses of the antifouling agent in a given crude oil sample in order to determine which dose is most effective for the crude oil. A sample of the crude oil is diluted with a quantity of an aromatic organic solvent. This mixture is thereafter equally subdivided into a plurality of vials. Into each vial is subsequently added a different dosage of the asphaltene dispersant antifouling agent being evaluated. A quantity from each vial is thereafter separately blended with a quantity of a liquid paraffinic hydrocarbon. The resulting blends are then maintained in an undisturbed environment thereby allowing the nondispersed material in the mixtures to settle, thus leaving a supernate containing dispersed materials. The concentration of dispersed materials is measured as the percent transmittance of light through a portion of the supernate from each mixture. The percent transmission of light through each sample is then compared to determine the optimum dosage of the antifouling agent in the crude oil. The optimum dosage is the lowest dosage of the asphaltene dispersant antifouling agent which disperses a sufficient quantity of asphaltene.

A further aspect of the present invention achieves the above results by providing a portable test kit to determine the optimal dose of a asphaltene dispersant antifouling agent necessary to add to a crude oil to alleviate the problem of asphaltene fouling of refinery equipment during the refining process. The test kit of the present invention includes a quantity of an aromatic organic solvent, a quantity of a liquid paraffinic hydrocarbon, a quantity of the antifouling agent solubilized in an aromatic inorganic solvent, and a photometer. The test kit is self contained, including all the components necessary to optimize the dosage of the antifouling agent.

BRIEF DESCRIPTION OF THE DRAWINGS

Other objects and advantages of the invention will become apparent upon reading the following detailed description and upon reference to the drawings.

DESCRIPTION OF THE PREFERRED EMBODIMENTS

Figure 1:
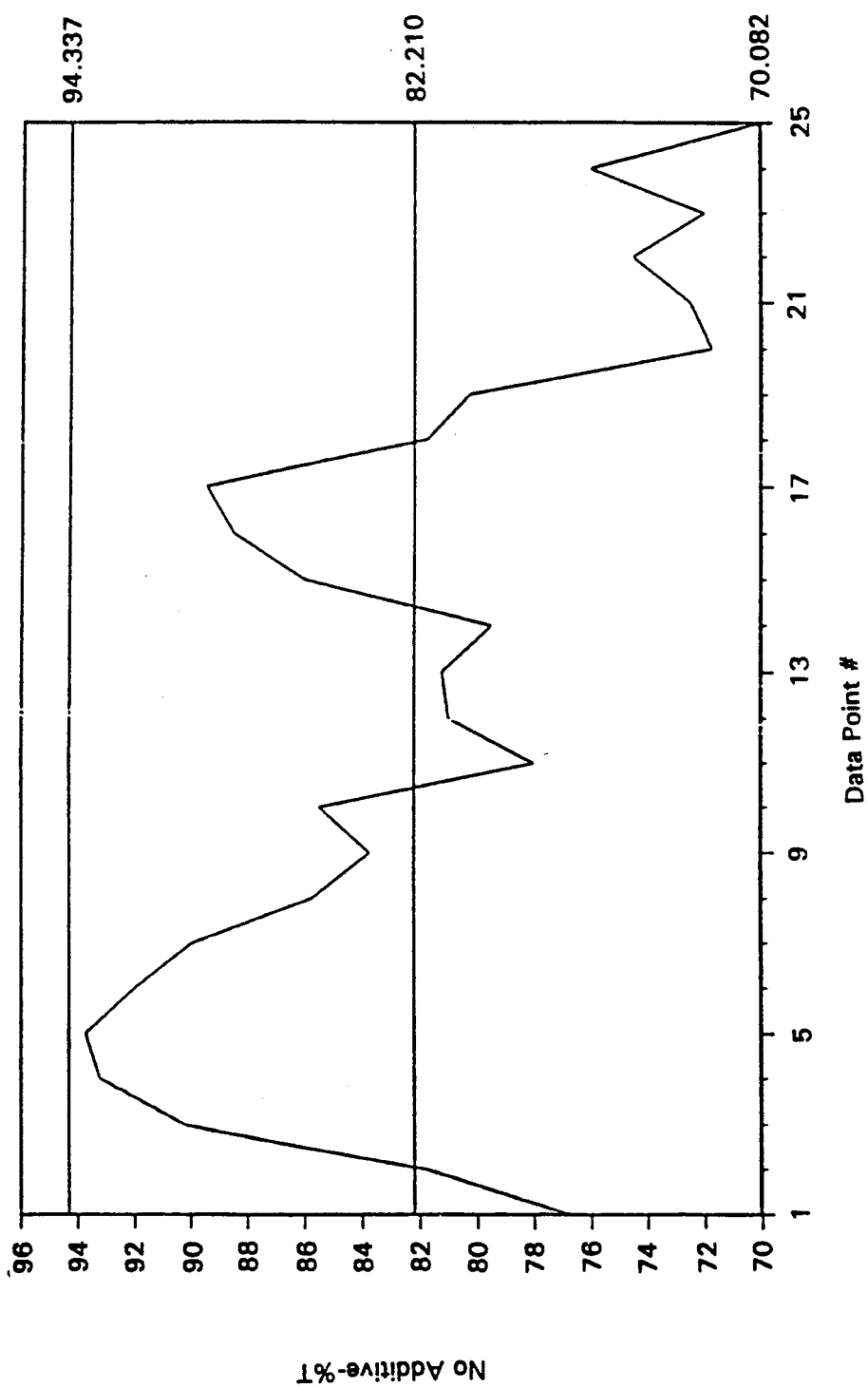
FIG. 1 shows the percent transmittance for the blank, Mini Spec 20 zeroed at 80% transmittance. Upper control limit is 94.337, mean is 82.210, and the lower control limit is 70.082. Control limits are plus or minus 14.8% from the mean.

The methods and test kit of the present invention are directed to providing the petroleum refinery industry a fast, inexpensive, reproducible, simple, and accurate method for optimizing the dosage of an asphaltene dispersant antifouling agent for a given crude oil containing asphaltenes.

One aspect of the present invention achieves these results by providing a method for evaluating the antifouling effectiveness of a dose of an asphaltene dispersant antifouling agents used in the oil refining process. According to one embodiment of the inventive method, a sample of the crude oil is diluted with a quantity of an aromatic organic solvent. To the diluted crude oil is added a known amount of the antifouling agent being evaluated. A portion of the diluted crude oil containing the antifouling agent is removed and mixed with a quantity of a liquid paraffinic hydrocarbon. The concentration of materials which remain dispersed in the liquid paraffinic hydrocarbon is thereafter measured. The above method is useful to evaluate a single dose of an antifouling agent or may be used to simultaneously evaluate a plurality of doses in order to determine which dose is most effective for a given sample of crude oil.

Another aspect of the present invention achieves the above results by providing a process for optimizing the dosage of an asphaltene dispersant antifouling agent in a crude oil containing asphaltenes by simultaneously evaluating a plurality of doses of the antifouling agent in a given crude oil sample in order to determine which dose is most effective for the crude oil. According to one embodiment of the inventive method, a sample of the crude oil is diluted with a quantity of an aromatic organic solvent. This mixture is thereafter subdivided into a plurality of vials. Into each vial is subsequently added a different dosage of the asphaltene dispersant antifouling agent being evaluated. A quantity from each vial is thereafter separately blended with a quantity of a liquid paraffinic hydrocarbon. The resulting blends are then maintained in an undisturbed environment thereby allowing the nondispersed material in the mixtures to settle, thus leaving a supernate containing dispersed materials. The concentration of dispersed materials is measured as the percent transmittance of light through a portion of the supernate from each mixture. The percent transmission of light through each sample is then compared to determine the optimum dosage of the antifouling agent in the crude oil. The optimum dosage being the lowest dosage of the asphaltene dispersant antifouling agent which disperses a sufficient quantity of asphaltene. Once the optimum dosage of the asphaltene dispersant has been calculated, an appropriate amount of asphaltene dispersant may then be added to the crude oil during the refining process in order alleviate the problem of asphaltene fouling of refinery equipment.

A further aspect of the present invention achieves the above results by providing a portable test kit which is intended for use by minimally-skilled refinery workers to determine the optimal dose of a asphaltene dispersant antifouling agent necessary to add to a crude oil to alleviate the problem of asphaltene fouling of refinery equipment during the refining process. Briefly, the test kit of the present invention includes a quantity of an aromatic organic solvent, a quantity of a liquid paraffinic hydrocarbon, a quantity of the antifouling agent solubilized in an aromatic inorganic solvent, and a photometer. The test kit is self contained, including all the components necessary to optimize the dosage of the antifouling agent. The test kit is preferably manufactured to be used at the refinery for continually monitoring the need for antifouling agents.

Aromatic organic solvents useful in the practice of the present invention are miscible with crude oil. More particularly, preferred aromatic organic solvents useful in the practice of the present invention are benzene, alkylbenzenes, polynuclear aromatic compounds, and alkyl substituted polynuclear aromatic compounds. More preferred aromatic organic solvents are benzene, toluene, naphthalene, alkylnaphthalenes, phenanthracene, and anthracene. Although many substituted derivatives of the above aromatic compounds may be useful in the practice of the present invention, the alkyl substituted aromatic compounds are the most preferred substituted aromatic organic solvents useful in the practice of the present invention. According to one embodiment, the aromatic organic solvent is utilized to dilute the crude oil sample in a volume ratio of from about 1:3 to about 3:1 crude oil/aromatic organic solvent. However, according to the most preferred embodiment, the aromatic organic solvent is utilized to dilute the crude oil sample in a volume ratio of 1:1.

Asphaltenes are not soluble to any appreciable extent in the liquid paraffinic hydrocarbons utilized in the practice of the present invention. The liquid paraffinic hydrocarbon is preferably an alkane. More preferably, the liquid paraffinic hydrocarbon is a straight chain alkane having a length of from about 5 to 17 carbon atoms. Most preferably, the liquid paraffinic hydrocarbon is a straight chain alkane having a length of from about 5 to 8 carbon atoms. The liquid paraffinic hydrocarbon of the present invention should be liquid at room temperature, and if used in the field, should be liquid at the temperature of the surrounding environment. Because the present invention will most likely be utilized in a variety of environments, the liquid paraffinic hydrocarbon may be varied in order to conform with the environment. For example, in an environment such as the oil fields of Alaska, a liquid paraffinic hydrocarbon having a carbon chain length of about 5 may be preferred. On the other hand, in warmer climates such as Texas, a paraffinic hydrocarbon having a carbon length of about 15 may be preferably employed. According to the most preferred embodiment, the liquid paraffinic hydrocarbon is N-hexane. The present inventor has determined that, based on the known physical properties, N-hexane would be the useful liquid paraffinic hydrocarbon for the widest range of environments.

When crude oil samples containing asphaltenes are blended with a quantity of the paraffinic hydrocarbon, the asphaltenes precipitate from the crude oil solution. If allowed, the precipitated asphaltenes would settle to the bottom of the container. This process mimics the agglomeration and precipitation of asphaltenes in the refining process. In the refining process, as asphaltenes are precipitated from the crude oil by heat, they agglomerate and precipitate onto the heated surfaces of oil refinery equipment. However, if the precipitated asphaltenes remain dispersed in the oil no fouling is seen. Thus, asphaltene dispersant antifouling agents are employed in the refining process to disperse the precipitated asphaltenes in the crude oil and thereby prevent the subsequent fouling of the oil refinery equipment.

One particularly useful class of asphaltene dispersant antifouling agents comprises polymeric asphaltene dispersants. Commercially, these agents are available from several companies which manufacture and sell oil field chemicals. Preferable antifoulant solutions include, an antifoulant solution including about 60% polyisobutenylsuccinimide in aromatic solvent, an antifoulant solution including about 33% polymethacrylate in aromatic solvent, Betz AF114, and Tretolite AF44. However, the most preferred asphaltene dispersant antifouling agent useful in the practice of the present invention is an antifoulant solution including 40% polyisobutenylsuccinate in aromatic solvent. Asphaltene antifoulant dispersing agents are generally added to the crude oil in a concentration of from about 10 to about 500 ppm.

The concentration of the material remaining dispersed in the liquid paraffinic hydrocarbon is measured in one preferred embodiment with a photometer. Photometers useful in the practice of the present invention preferably read and record the percent transmittance of light through a sample in the wavelength ranges of from about 520 to 740 nm. Indeed it has been determined through experimentation that an especially preferred wavelength of light measured is about 640 nm. As seen in following Example 2, the inventor measured several wavelengths of light passed through several samples of crude oil. This was done to test each crude oil's individual response to different wavelengths of light. It was found that for the crude oils tested, the most useful wavelength was 640 nm. This wavelength gave a broad spread of responses for percent transmittance over the dosages of antifouling agents tested. Higher wavelengths forced the response curve too high on transmittance; lower wavelengths forced the response curve too low. Although several commercially available photometers may be utilized in the practice of the present invention, the most preferred photometers are the Nalco Mini Spec 200 and the Nalco Digidisk Photometer.

The methods of the present invention ar useful for determining the effectiveness of a single dose of an antifouling agent or for determining the optimum dose of an antifouling agent by simultaneously assaying a plurality of different dosages of the antifouling agent. According to one preferred embodiment, the method of the present invention is utilized to assay the effectiveness of a single dose of an antifouling agent in a given crude oil sample. According to the embodiment, a crude oil sample is thoroughly mixed with an aromatic organic solvent to form a first mixture. Experimentation has determined that the preferred ratio of crude oil to organic aromatic solvent in the first mixture is about 1:1. To the first mixture a sufficient amount of a asphaltene dispersant antifouling agent is added to form a second mixture. Preferably the asphaltene dispersant antifouling agent is added to the first mixture as a 10% solution of the antifouling agent in an aromatic organic solvent. The asphaltene dispersant antifouling agent is added to the first mixture in such an amount such that the resulting concentration of the antifoulant agent in the second mixture is from about 10 to about 500 ppm, and most preferably, from about 5 to about 50 ppm.

A portion of the second mixture is subsequently added to a container containing a liquid paraffinic hydrocarbon to form a third mixture. Experimentation has determined that the portion of the second mixture added to the liquid paraffinic hydrocarbon preferably includes from about 37.5 to about 75 microliters of the crude oil per each 10 ml of the liquid paraffinic hydrocarbon. According to experimental evidence, the present inventor determined that the preferred amount of crude oil added to each 10 ml of the liquid paraffinic hydrocarbon is about 50 microliters. When the third mixture contained 37.5 microliters or less of crude oil per each 10 ml of the liquid paraffinic hydrocarbon no performance breaks were observed for the different dosages of the antifouling agent assayed. The shape of the performance curves obtained were inverted, exponential curves, showing 100% dispercancy at low dosage and then no further performance improvement. Thus, it was determined by the present inventor that 37.5 microliters or less of crude oil in 10 ml of the third mixture yielded unsatisfactory results. Further, the present inventor determined that 75 microliters or greater of crude oil included in each 1 ml of the third mixture yielded unsatisfactory results. The present inventor determined that when the third mixture was loaded too heavy with crude oil, the performance profile of the antifouling agent, in the 0 to 50 ppm range tested, showed no performance breaks for the antifouling agent tested. The shape of the performance curve was linear or a smooth decline, still declining at the upper dosage of 50 ppm. This showed that increasing dosages of chemical continued to show improvement performance but 100% dispercancy was not seen even at the upper limit of testing. An analogous method of expressing the above is that the preferred volume ratio of crude oil to liquid paraffinic hydrocarbon in the mixture is from about 1:125 to about 1:275, and most preferably about 1:200.

After the third mixture is thoroughly blended, it is allowed to stand for approximately 1 to about 3 hours, and more preferably, about 2 hours. After a sufficient amount of time has elapsed, the top few milliliters of liquid is drawn from the third mixture and delivered into a photometer vial. Preferably, the photometer is set at a wavelength of from about 520 to about 740 nm, and more preferably, at a wavelength of about 640 nm. The photometer is zeroed to 100% transmittance using an untreated sample. The transmittance of light is read and recorded by the photometer for the sample being assayed. The percent of light transmittance being inversely proportional to the effectiveness of a given dose of the antifouling agent.

As discussed above, determining the optimum dose of antifouling agent added to the crude oil is crucial to the efficient refining of crude oil. According to a preferred embodiment, the inventive method is utilized to simultaneously assay a plurality of antifouling agent dosages in order to determine the optimum dosage of the antifouling agent for a particular crude oil. According to the preferred embodiment, an equal volume of a crude oil and an aromatic organic solvent, preferably toluene, are thoroughly mixed. The resulting solution is divided into six 20 ml samples. An asphaltene dispersing antifouling agent, most preferably an antifoulant solution including 40% polyisobutenylsuccinate in aromatic solvent, is added to an aromatic organic solvent, preferably as a 10% (volume/volume) solution. The 10% antifouling agent solution is added to five of the 20 ml samples at dosages of 5 ppm, 10 ppm, 15 ppm, 25 ppm, and 50 ppm (volume/volume ratio). The solutions are thoroughly mixed. Using a microsyringe, a portion from each sample is thereafter added to a separate vial containing a liquid paraffinic hydrocarbon. Preferably, the liquid paraffinic hydrocarbon is hexane. Preferably, the portion of each sample added to the liquid paraffinic hydrocarbon includes from about 37.5 to about 75 milliters of the crude oil per each 10 ml of the liquid paraffinic hydrocarbon, and most preferably, about 50 microliters. The vials are capped and shaken vigorously to ensure mixing. The vials are placed in a rack and are allowed to remain undisturbed preferably for approximately two hours. After this period, the top few milliliters of each vial are removed and delivered into a photometer vial. The photometer is set at from about 520 to about 740 nm, and most preferably at 640 nm wavelength. The photometer is zeroed at 100% transmittance using the untreated sample. The photometer subsequently reads and records the percent transmittance of light through each of the samples. The lower the percent transmittance of light through the solution, the more effective the particular dose of the antifouling agent. Therefore, the percentage transmittance of light through a sample is inversely proportional to the effectiveness of a given dosage of the antifouling agent.

The following examples are presented to describe preferred embodiments and utilities of the present invention and are not meant to limit the present invention unless otherwise stated in the claims appended hereto.

EXAMPLES

Example 1

Example 1 demonstrates the reproducability of the inventive method. A series of repetitive samples were set up and measured. Five dosages of an antifoulant solution including 40% polyisobutenylsuccinate in aromatic solvent and a control were evaluated. This series was repeated 25 times. The results were input into a statistical analysis program. They showed that every sample prepared yielded statistically the same percent transmittance, plus or minus 15-20% around the mean.

According to the procedure for Example 1, approximately 150 ml of crude oil was added to 50 ml of toluene in an 8 oz. bottle. The solution was shaken until thoroughly mixed. The crude oil/toluene solution was divided into nine 20 ml samples using 20 ml scintillation vials. Six samples were used, the other three were discarded. A 10% solution of the asphaltene dispersing antifouling agent in toluene (volume/volume) was prepared. The 10% solution of the polyisobutenylsuccinate was added to five of the 20 ml crude oil/toluene samples. The 10% solution of the antifoulant was added in dosages of 5, 10, 15, 25, and 50 ppm (volume/volume ratio). The vials were shaken for approximately 15 seconds to insure proper mixing. For each 20 ml crude oil/toluene sample, the following table shows the amount of dispersant antifouling solution added for proper dosage:

| Dosage of Antifoulant | Microliters of 10% Antifoulant Solution |
| --- | --- |
| 5 ppm | 1 microliter |
| 10 ppm | 2 microliter |
| 15 ppm | 3 microliter |

-continued

| Dosage of Antifoulant | Microliters of 10% Antifoulant Solution |
|---|---|
| 25 ppm | 5 microliter |
| 50 ppm | 10 microliter |

Using a 500 microliter syringe, 50 microliters of each crude oil/toluene/antifoulant sample was added to a centrifuge tube containing 10 ml of hexane. Each tube was capped and shaken vigorously for approximately 10 seconds until well mixed. The tubes were thereafter placed in a test tube rack, where they were left undisturbed for approximately two hours. After two hours, the top 2 milliliters of liquid was removed with a pipet from each centrifuge tube and deliver into a photometer vial.

The photometer, a Nalco Mini Spec 20, was set to record the percent of light transmittance having a 640nm wavelength and was zeroed at 100% transmission using the untreated sample. The percent transmission for each of the samples was read and recorded. The above procedure was repeated twenty-five times.

Figure 2:
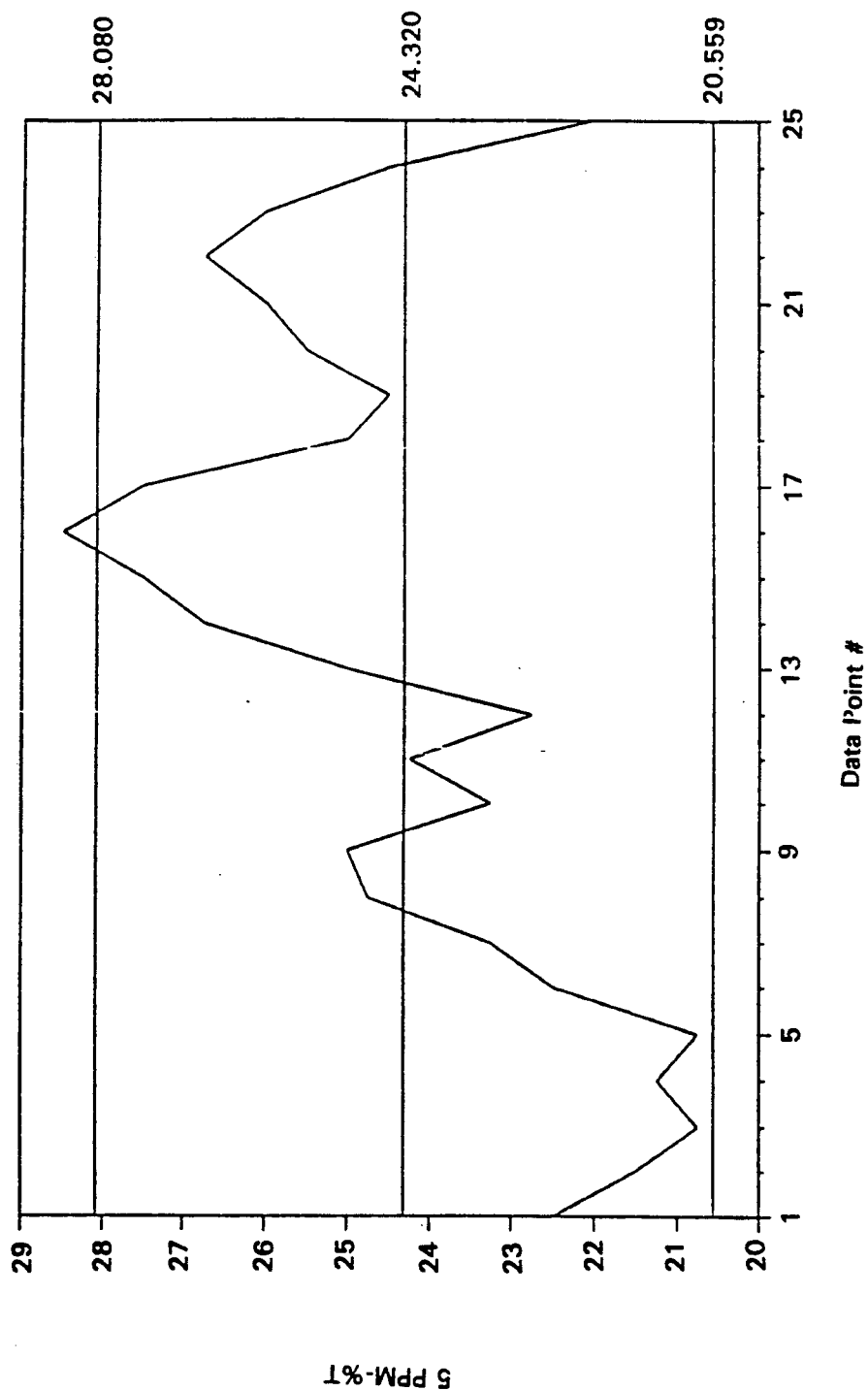
FIG. 2 shows the percent transmittance for 5 ppm of an antifoulant solution including 40% polyisobutenylsuccinate in aromatic solvent, Mini Spec 20 zeroed at 100% transmittance. Upper control limit is 28.080, mean is 24.320, and the lower control limit is 20.559. Control limits are plus or minus 15.5% from the mean.
Figure 3:
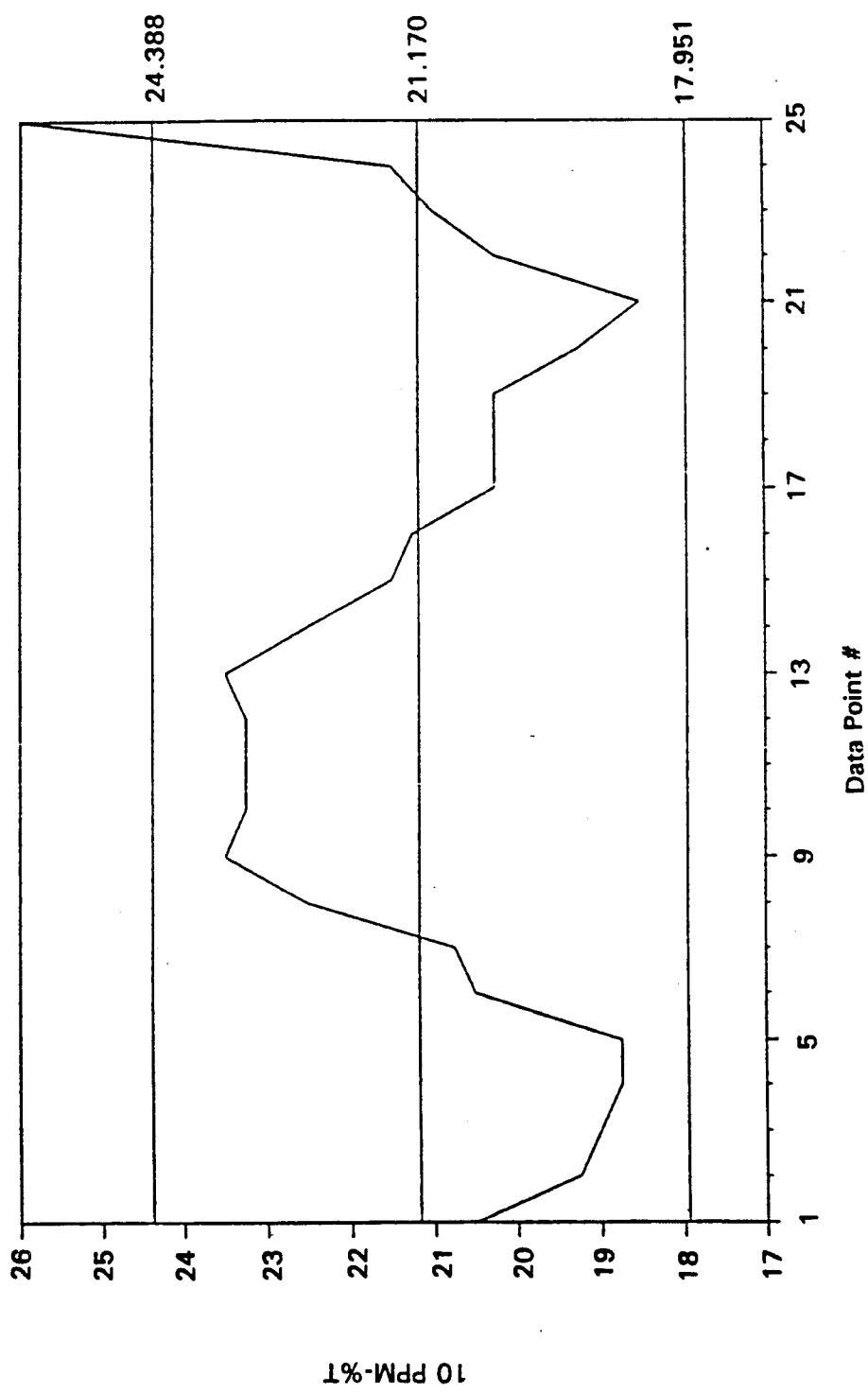
FIG. 3 shows the percent transmittance for 10 ppm of an antifoulant solution including 40% polyisobutenylsuccinate in aromatic solvent, Mini Spec 20 zeroed at 100% transmittance. Upper control limit is 24.388, mean is 21.170, and the lower control limit is 17.951. Control limits are plus or minus 15.2% from the mean.
Figure 4:
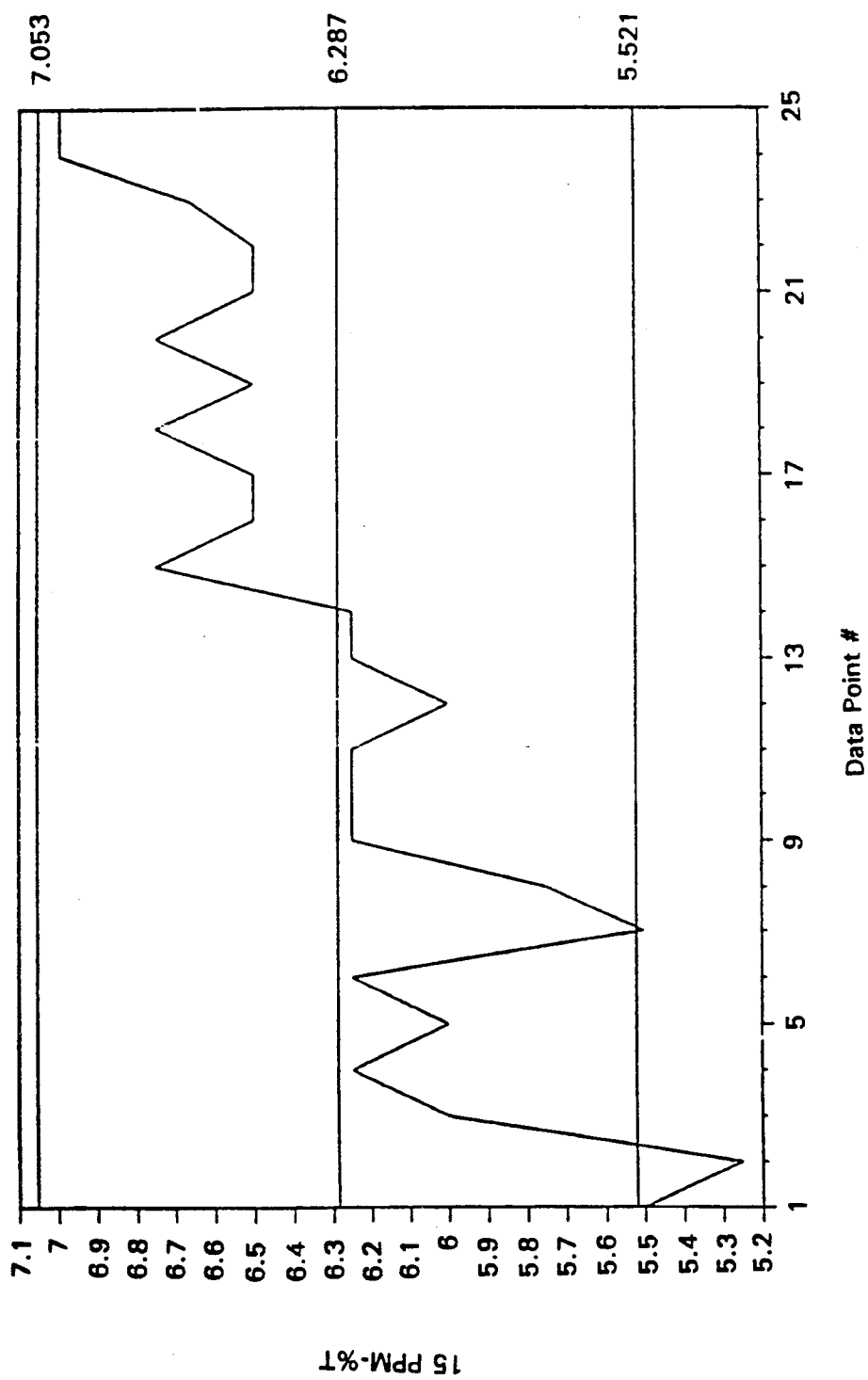
FIG. 4 shows the percent transmittance for 15 ppm of an antifoulant solution including 40% polyisobutenylsuccinate in aromatic solvent, Mini Spec 20 zeroed at 100% transmittance. Upper control limit is 7.053, mean is 6.287, and the lower control limit is 5.521. Control limits are plus or minus 12.2% from the mean.
Figure 5:
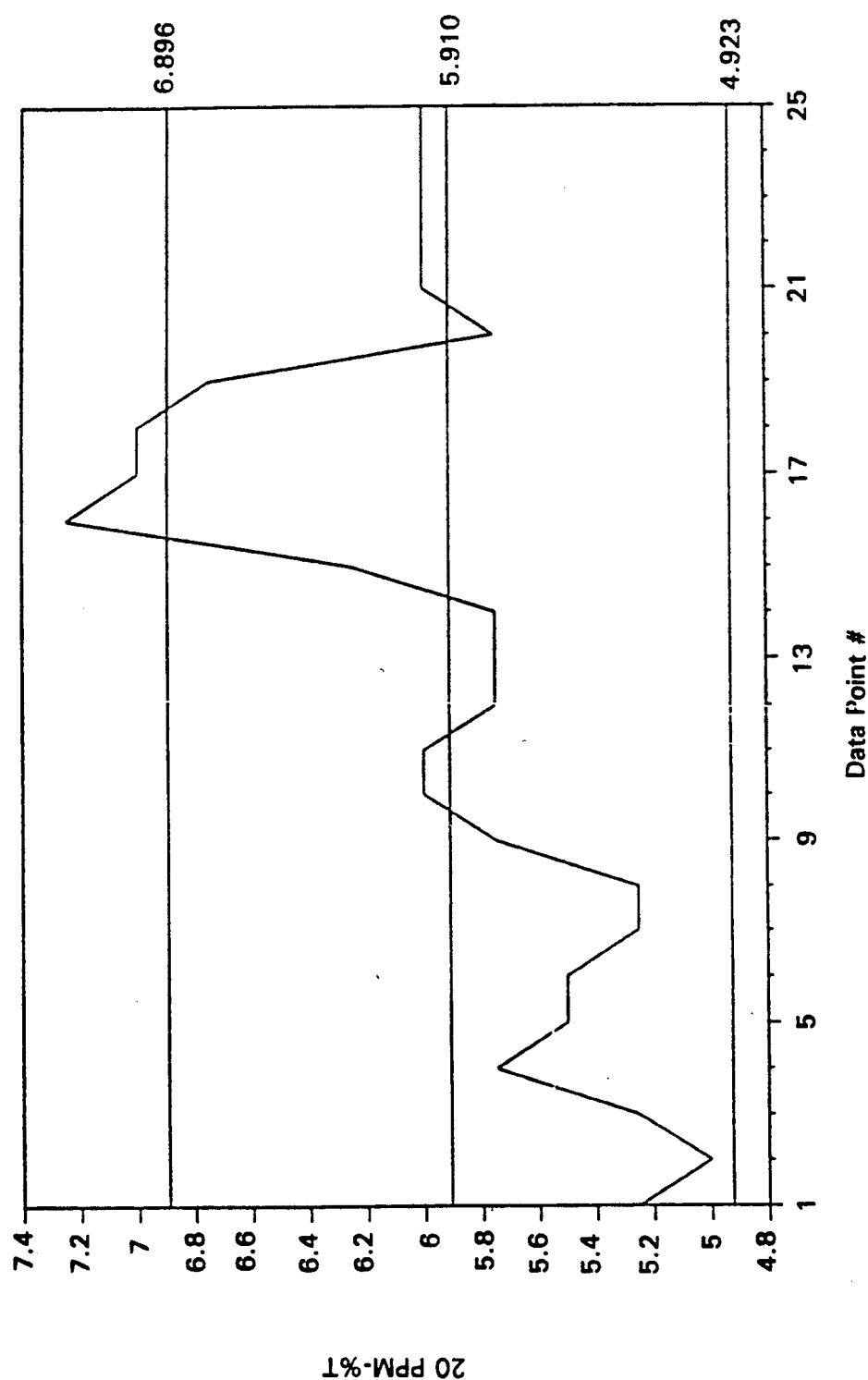
FIG. 5 shows the percent transmittance for 20 ppm of an antifoulant solution including 40% polyisobutenylsuccinate in aromatic solvent, Mini Spec 20 zeroed at 100% transmittance. Upper control limit is 6.896, mean is 5.910, and the lower control limit is 4.923 Control limits are plus or minus 16.7% from the mean.
Figure 6:
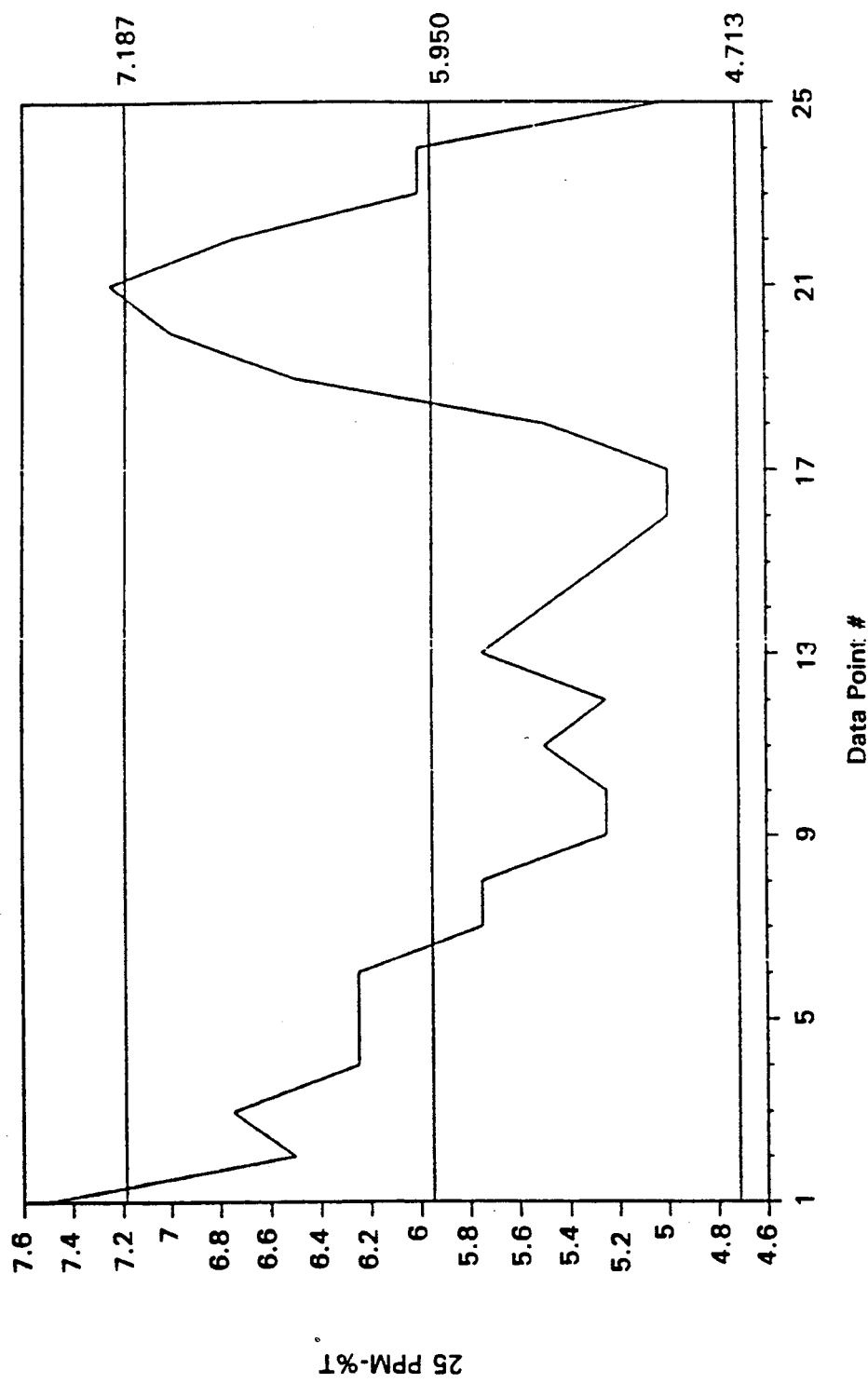
FIG. 6 shows the percent transmittance for 25 ppm of an antifoulant solution including 40% polyisobutenylsuccinate in aromatic solvent, Mini Spec 20 zeroed at 100% transmittance. Upper control limit is 7.187, mean is 5.950, and the lower control limit is 4.713. Control limits are plus or minus 20.8% from the mean.
Figure 7:
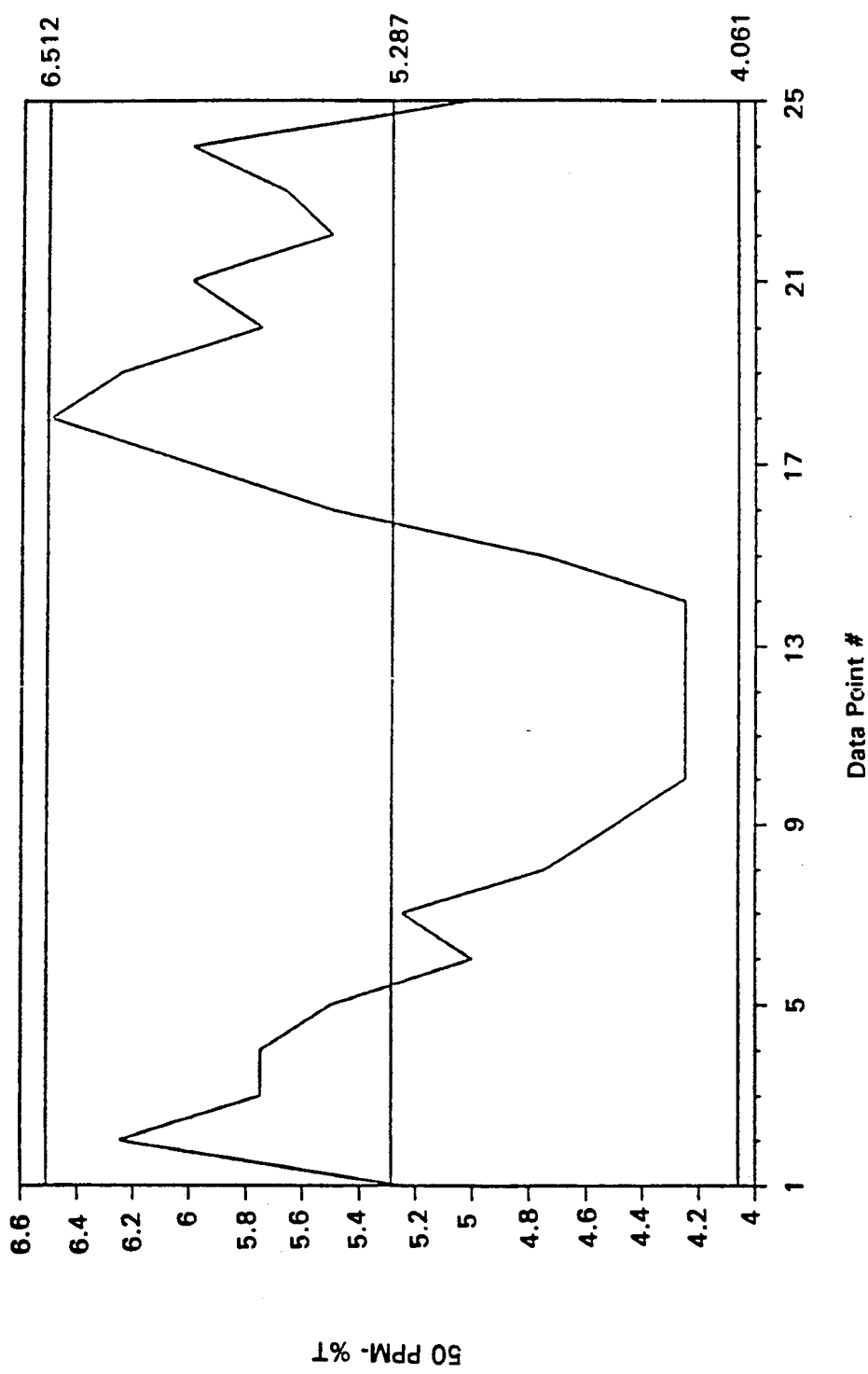
FIG. 7 shows the percent transmittance for 50 ppm of an antifoulant solution including 40% polyisobutenylsuccinate in aromatic solvent, Mini Spec 20 zeroed at 100% transmittance. Upper control limit is 6.512, mean is 5.287, and the lower control limit is 4.061. Control limits are plus or minus 23.2% from the mean.

The data obtained was entered into a Lotus template for SPC calculations and X-Bar charts were created. These charts are presented as FIGS. 1-7. It was found that the deviation from the mean, ±3 standard deviations, was about 15% in each case tested. Restated, the test method for preparing samples can be reproduced 99.7% of the time to within about 15%. This is an acceptable tolerance for field test methods and kits. The data obtained is summarized in Table I below.

In Example 1, 50 microliters of crude oil/toluene solution was added to the centrifuge tubes containing hexane; however, In Example 2, 50, 100, 200, and 250 microliters of the crude oil/toluene solution was added to the centrifuge tubes containing hexane in order to determine the optimum volume and amount of crude oil (feedstock) to add to the hexane.

In Example 1, crude oil from a single source was used; however, In Example 2, three sources of crude oil (feedstock) were used, identified as crude oil A, crude oil B, and crude oil C, in order to determine the effectiveness of the inventive method in several distinct crude oils (feedstock).

In Example 1, the photometer was set to read light transmittance at a wavelength of 640 nm; however, In Example 2, separate trials were conducted with the photometer set at wavelengths of 520 nm, 560 nm, 600 nm, 640 nm, 680 nm, and 720 nm in order to determine the most efficient wavelength to measure the percent of light transmitted through the sample.

Figure 11:
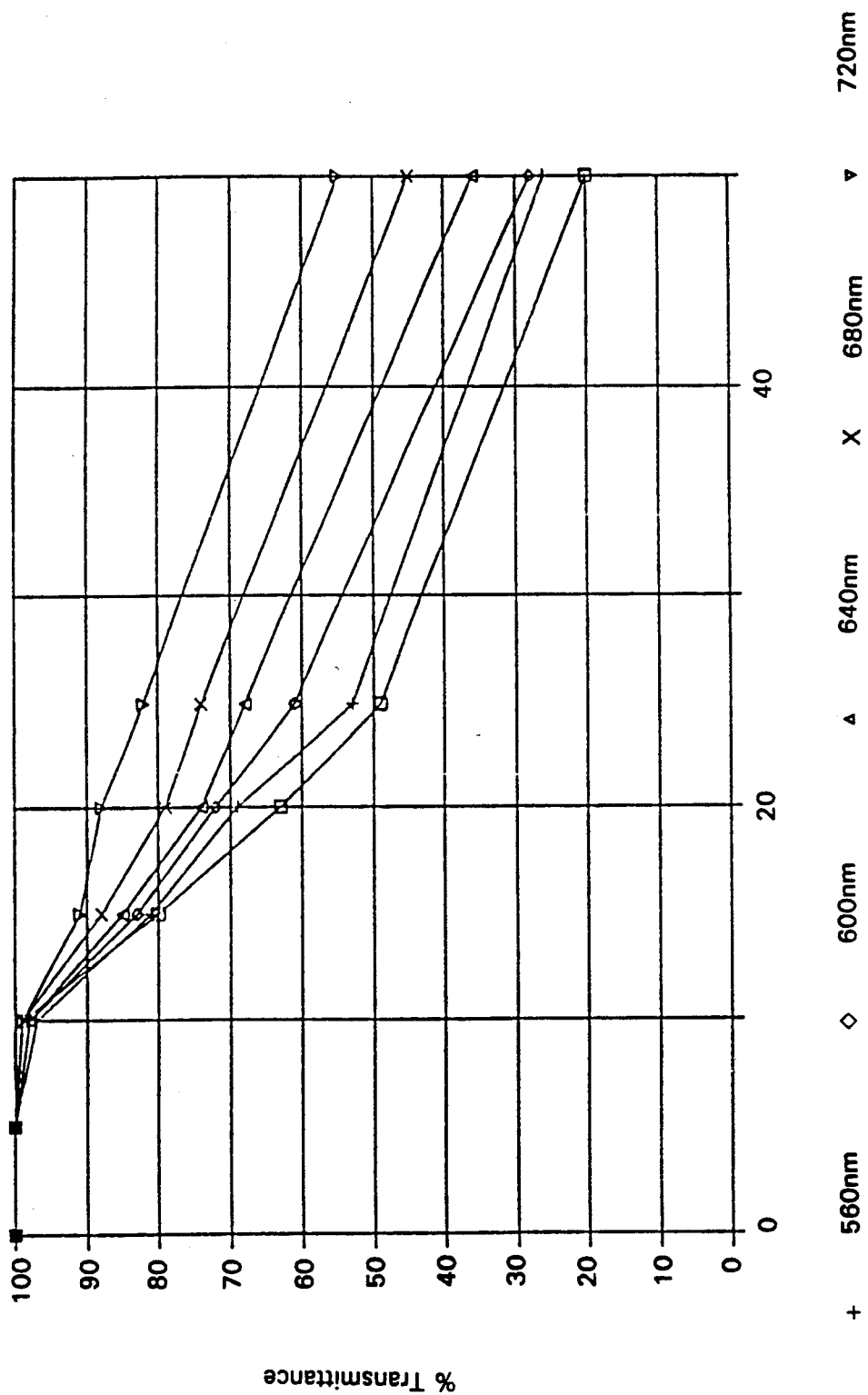
FIG. 11 shows the percent transmittance of varied wavelengths of light for varied dosages of an antifoulant solution including 40% polyisobutenylsuccinate in aromatic solvent for crude oil A 50%, 200 microliter stock.
Figure 15:
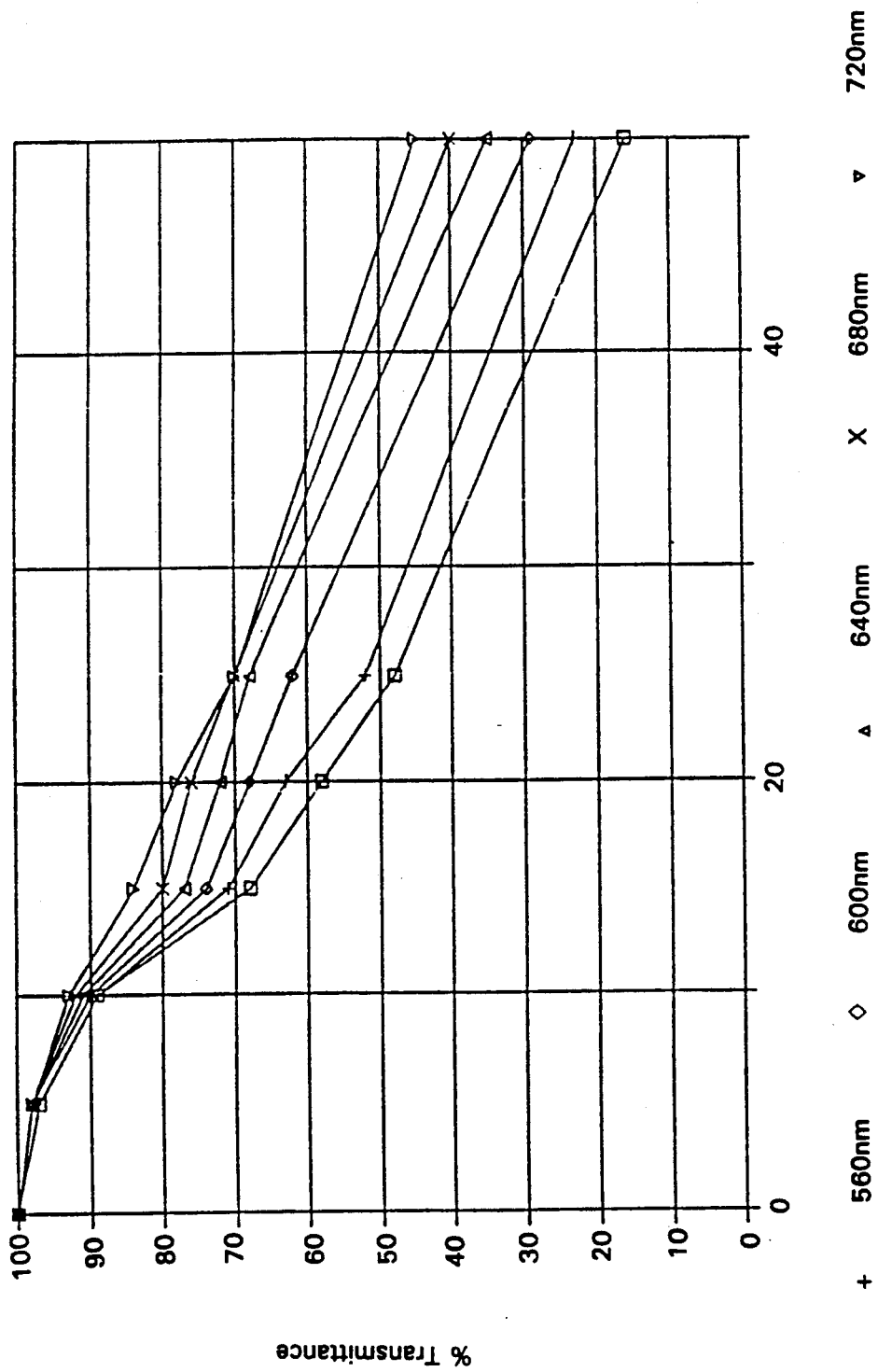
FIG. 15 shows the percent transmittance of varied wavelengths of light for varied dosages of an antifoulant solution including 40% polyisobutenylsuccinate in aromatic solvent for crude oil B 50%, 200 microliter stock.
Figure 19:
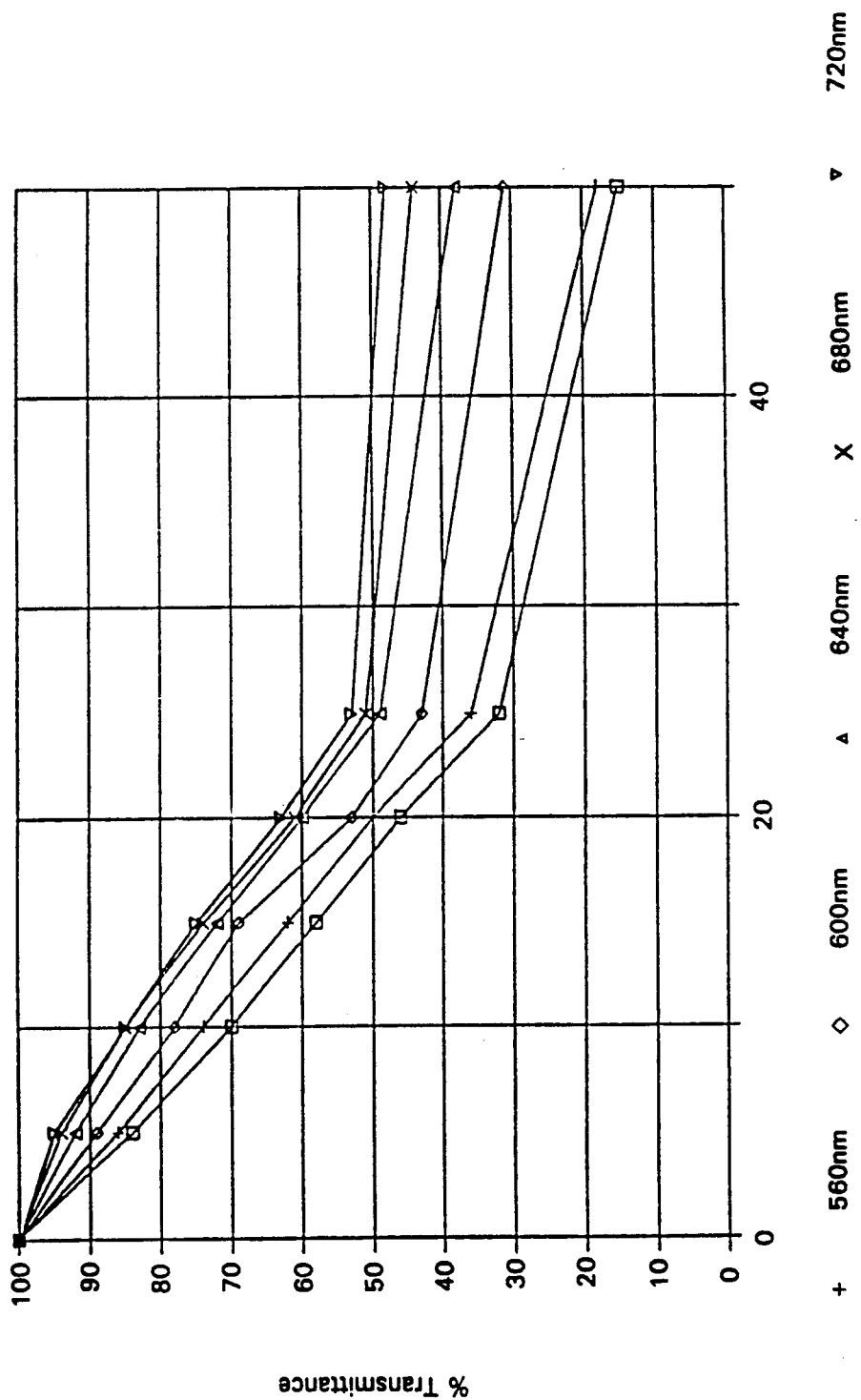
FIG. 19 shows the percent transmittance of varied wavelengths of light for varied dosages of an antifoulant solution including 40% polyisobutenylsuccinate in aromatic solvent for crude oil C 50%, 200 microliter stock.
Figure 21:
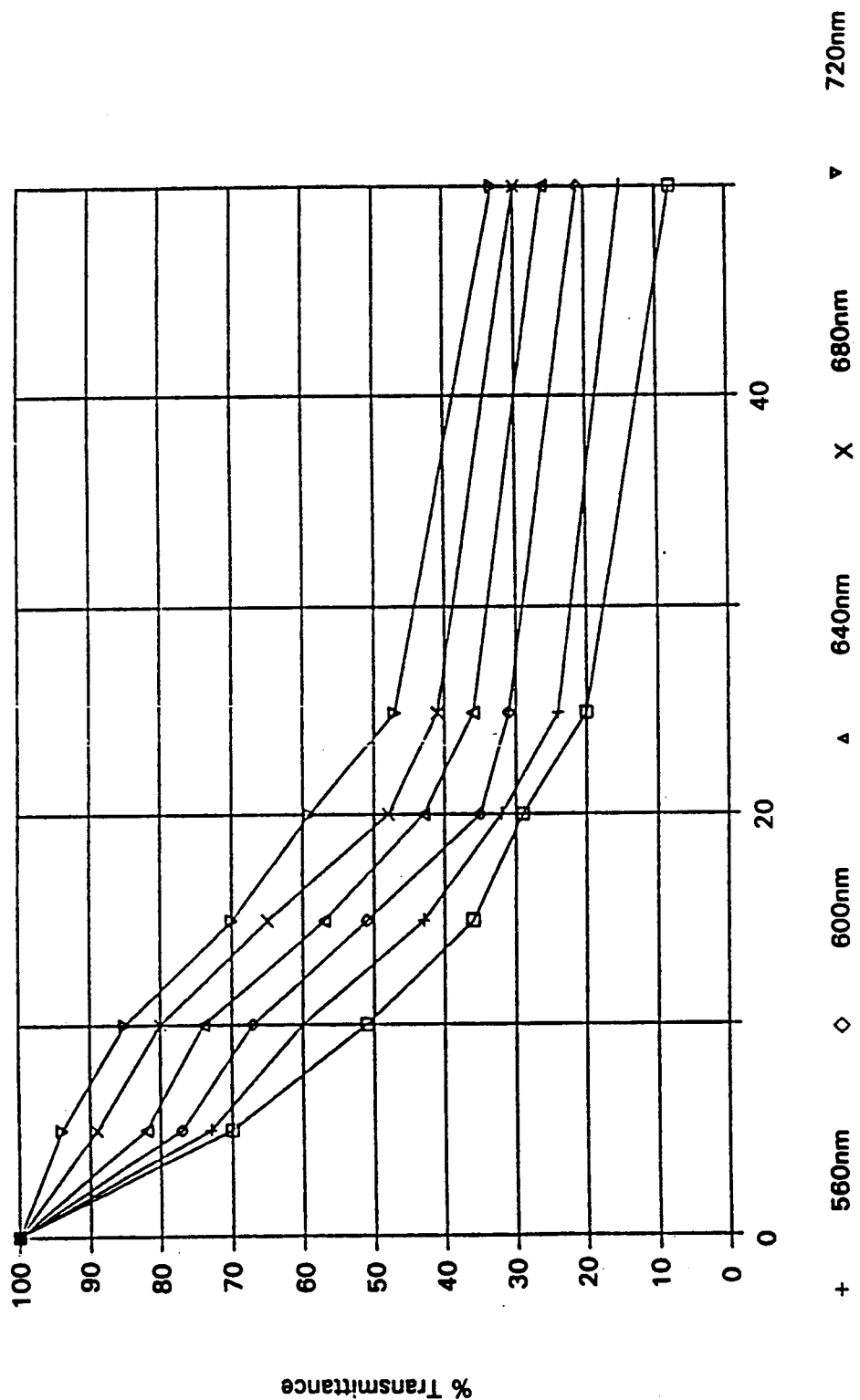
FIG. 21 shows the percent transmittance of varied wavelengths of light for varied dosages of an antifoulant solution including 40% polyisobutenylsuccinate in aromatic solvent for crude oil B 75%, 100 microliter stock.

In Example 2 it was determined that when the system was loaded too heavy with crude oil, the performance profile of the antifouling agent, in the zero to 50 ppm range tested, tends to show no performance breaks for the antifouling agent being assayed. As shown in FIGS. 11, 15, 19, and 21, the shape of the performance curve is linear or a smooth decline, still declining at the upper dosage of 50 ppm. This shows that increasing dosages of chemical continue to show improved performance but 100% dispersancy is not seen even at the upper limit of testing. If the concentration of the dilute crude oil is multiplied by the number of microliters added to the

TABLE I

| Data Point | Blank % T | 5 PPM % T | 10 PPM % T | 15 PPM % T | 20 PPM % T | 25 PPM % T | 50 PPM % T |
|---|---|---|---|---|---|---|---|
| 1 | 80.00 | 26.00 | 22.00 | 6.00 | 6.00 | 10.00 | 4.00 |
| 2 | 66.00 | 24.00 | 22.00 | 5.00 | 5.00 | 6.00 | 5.00 |
| 3 | 81.00 | 19.00 | 19.00 | 5.00 | 5.00 | 8.00 | 6.00 |
| 4 | 80.00 | 21.00 | 19.00 | 6.00 | 5.00 | 6.00 | 6.00 |
| 5 | 100.00 | 22.00 | 17.00 | 5.00 | 5.00 | 6.00 | 8.00 |
| 6 | 100.00 | 21.00 | 21.00 | 8.00 | 6.00 | 7.00 | 3.00 |
| 7 | 93.00 | 21.00 | 18.00 | 6.00 | 7.00 | 6.00 | 6.00 |
| 8 | 82.00 | 19.00 | 19.00 | 5.00 | 4.00 | 6.00 | 5.00 |
| 9 | 93.00 | 29.00 | 24.00 | 6.00 | 5.00 | 6.00 | 6.00 |
| 10 | 92.00 | 24.00 | 22.00 | 5.00 | 5.00 | 5.00 | 4.00 |
| 11 | 76.00 | 27.00 | 25.00 | 7.00 | 7.00 | 6.00 | 4.00 |
| 12 | 74.00 | 20.00 | 23.00 | 7.00 | 6.00 | 4.00 | 4.00 |
| 13 | 100.00 | 22.00 | 23.00 | 6.00 | 6.00 | 6.00 | 5.00 |
| 14 | 62.00 | 28.00 | 22.00 | 5.00 | 5.00 | 6.00 | 4.00 |
| 15 | 88.00 | 21.00 | 25.00 | 6.00 | 6.00 | 5.00 | 4.00 |
| 16 | 75.00 | 29.00 | 24.00 | 8.00 | 6.00 | 6.00 | 4.00 |
| 17 | 93.00 | 29.00 | 19.00 | 6.00 | 6.00 | 5.00 | 5.00 |
| 18 | 88.00 | 31.00 | 18.00 | 7.00 | 7.00 | 5.00 | 6.00 |
| 19 | 98.00 | 25.00 | 24.00 | 5.00 | 10.00 | 4.00 | 7.00 |
| 20 | 79.00 | 25.00 | 20.00 | 8.00 | 5.00 | 6.00 | 6.00 |
| 21 | 62.00 | 19.00 | 19.00 | 7.00 | 6.00 | 7.00 | 7.00 |
| 22 | 82.00 | 29.00 | 18.00 | 6.00 | 6.00 | 9.00 | 5.00 |
| 23 | 64.00 | 29.00 | 20.00 | 6.00 | 6.00 | 6.00 | 5.00 |
| 24 | 82.00 | 27.00 | 17.00 | 7.00 | 6.00 | 6.00 | 5.00 |
| 25 | 70.00 | 22.00 | 26.00 | 7.00 | 6.00 | 5.00 | 5.00 |

EXAMPLE 2

Example 2 consisted of several trials. Each trial followed the protocol set forth for in Example 1 except for the following listed exceptions.

In Example 1, a 75% crude oil solution was used; however, Example 2, utilized 25, 50 and 75% crude oil solutions in order to determine the optimal amount of crude oil, also referred to as feedstock, used in the practice of the present invention.

centrifuge tube, the result is the actual concentration of crude oil. Heavy loading as described above is a concentration of 75 or more microliters of crude oil (for example, 100 microliters of a 75% dilute solution of crude oil equals 75 microliters of crude oil) per each 10 ml of the liquid paraffinic hydrocarbon, i.e., hexane.

Figure 8:
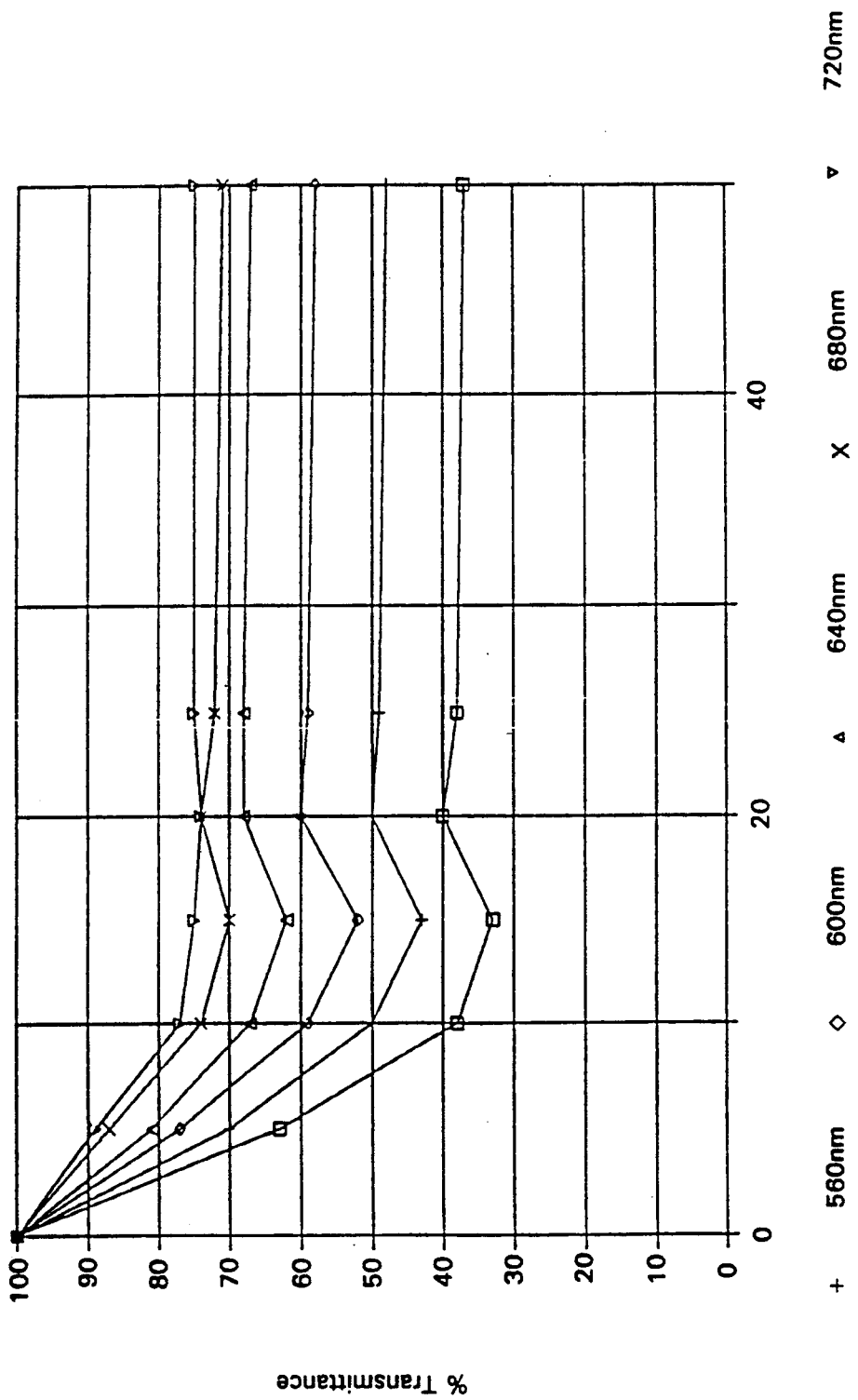
FIG. 8 shows the percent transmittance of varied wavelengths of light for varied dosages of an antifoulant solution including 40% polyisobutenylsuccinate in aromatic solvent for crude oil A 25%, 100 microliter stock.
Figure 12:
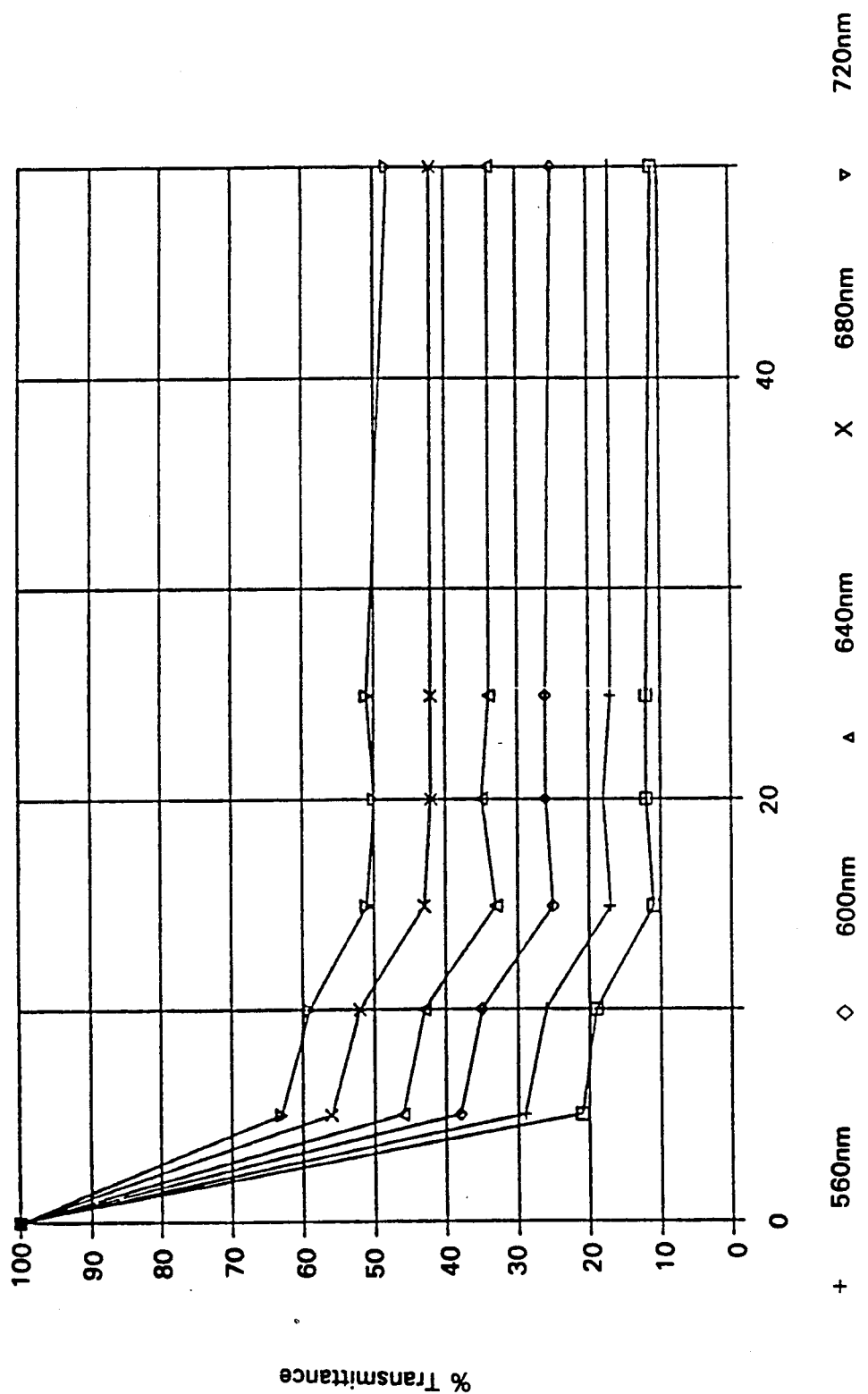
FIG. 12 shows the percent transmittance of varied wavelengths of light for varied dosages of an antifoulant solution including 40% polyisobutenylsuccinate in aromatic solvent for crude oil B 25%, 100 microliter stock.
Figure 16:
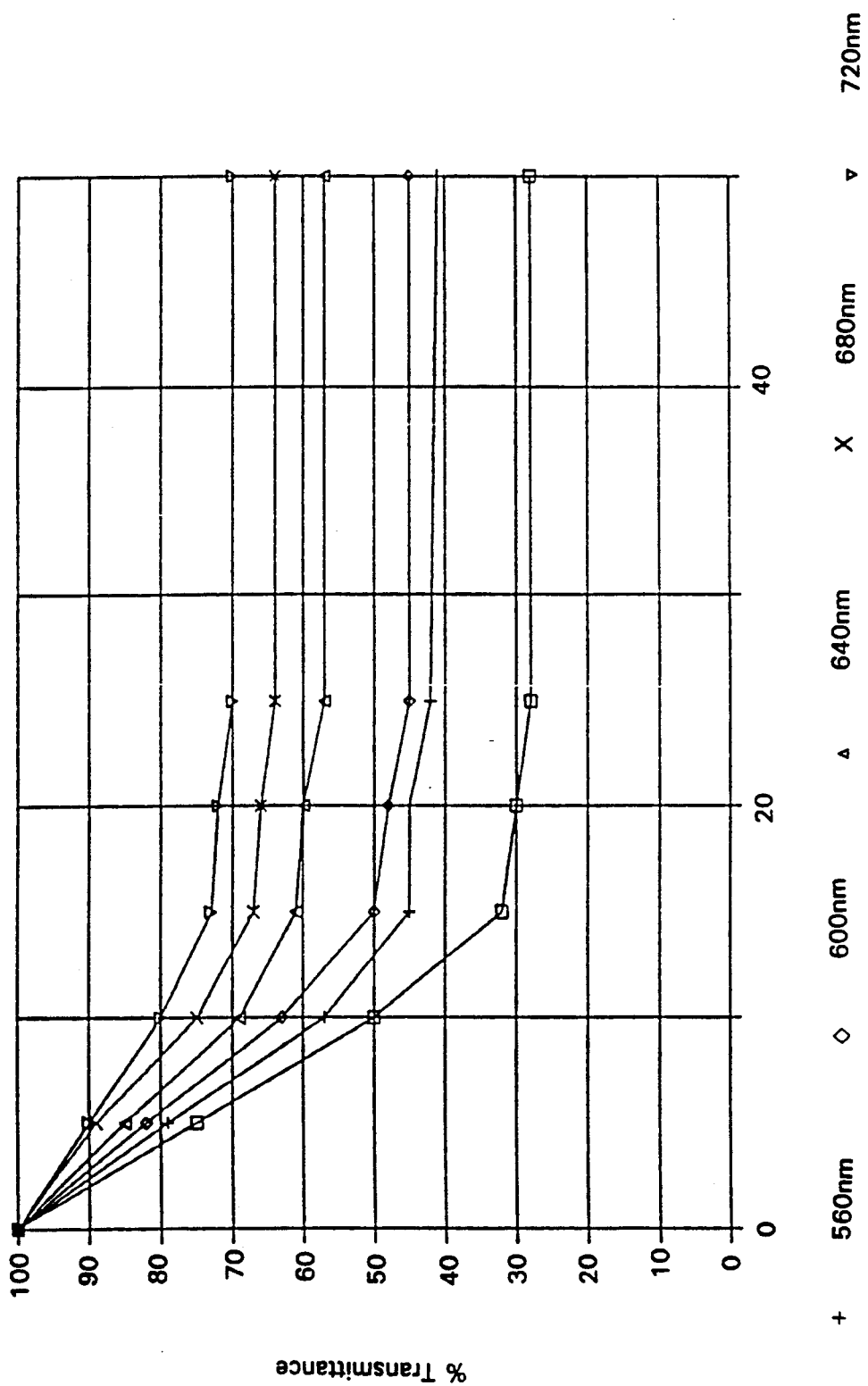
FIG. 16 shows the percent transmittance of varied wavelengths of light for varied dosages of an antifoulant solution including 40% polyisobutenylsuccinate in aromatic solvent for crude oil C 25%, 100 microliter stock.
Figure 20:
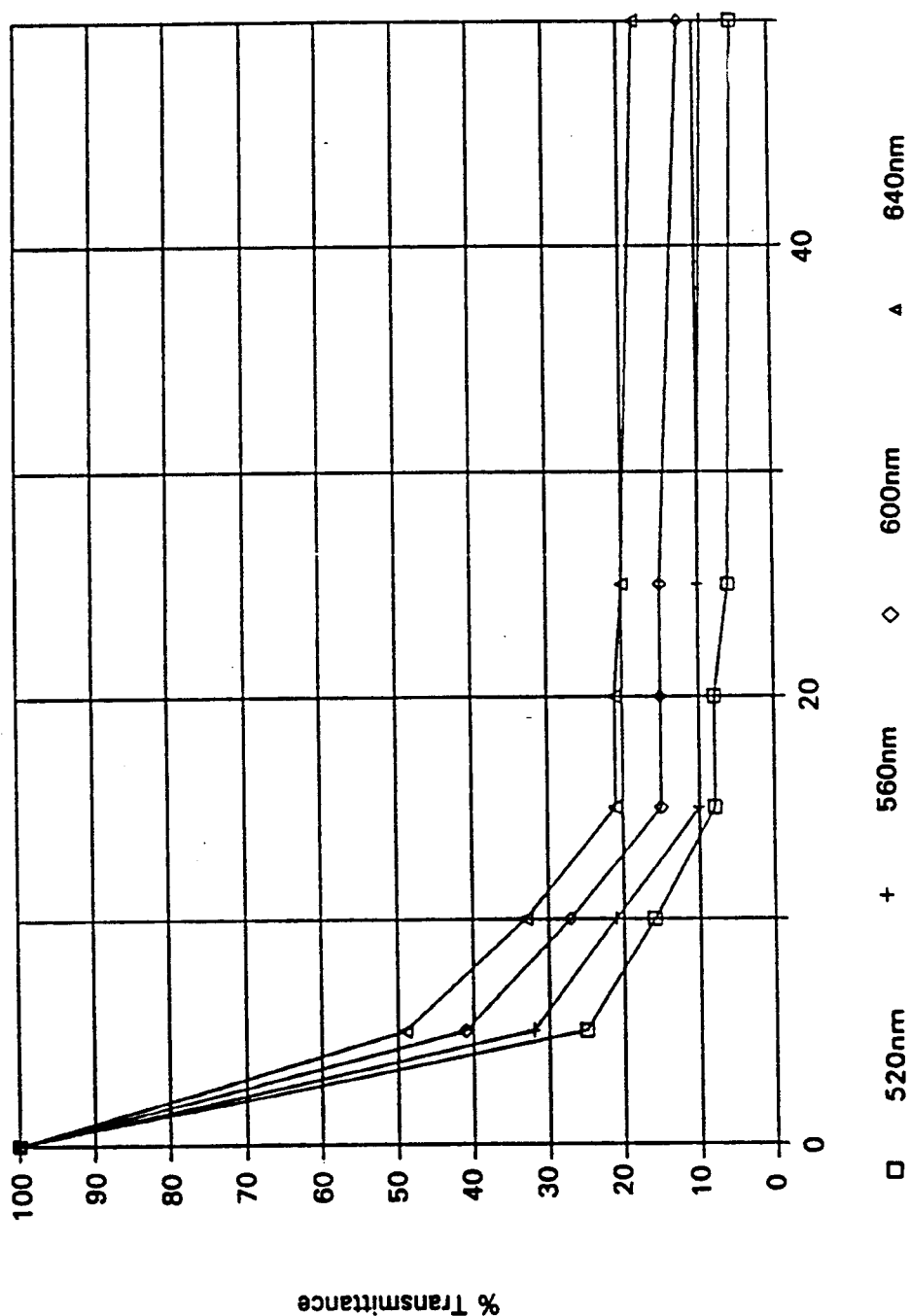
FIG. 20 shows the percent transmittance of varied wavelengths of light for varied dosages of an antifoulant solution including 40% polyisobutenylsuccinate in aromatic solvent for crude oil B 75%, 50 microliter stock.

If the system was loaded too light with crude oil, again no performance breaks were detected. As shown In FIGS. 8, 12, 16, and 20, the shape of these curves was an inverse expediential curve, showing that almost 100% dispersancy at low dosage and no further performance improvement. In this case, 37.5 microliters or less of crude oil per 10 ml of Hexane was too light. The most preferred amount of crude oil for this method was found to be about 50–62.5 microliters of crude oil per each 10 ml of Hexane for the several samples tested. Hence, the preferred test method procedures utilize a 50% dilution of the crude oil dosed into the centrifuge tube at 100 microliters per 10 ml of liquid paraffinic hydrocarbon.

As discussed above, several wavelengths of light were tested for each sample. This was done to test each crude oil for its individual response to different wavelengths. It was found that for the crude oils tested, the most preferred wavelength was 640 nm. This wavelength gave a broad spread of response for transmittance over the dosages of antifouling agent tested. Higher wavelengths of light forced the transmission response curves too high; lower wavelengths forced the transmission curve too low.

Figure 9:
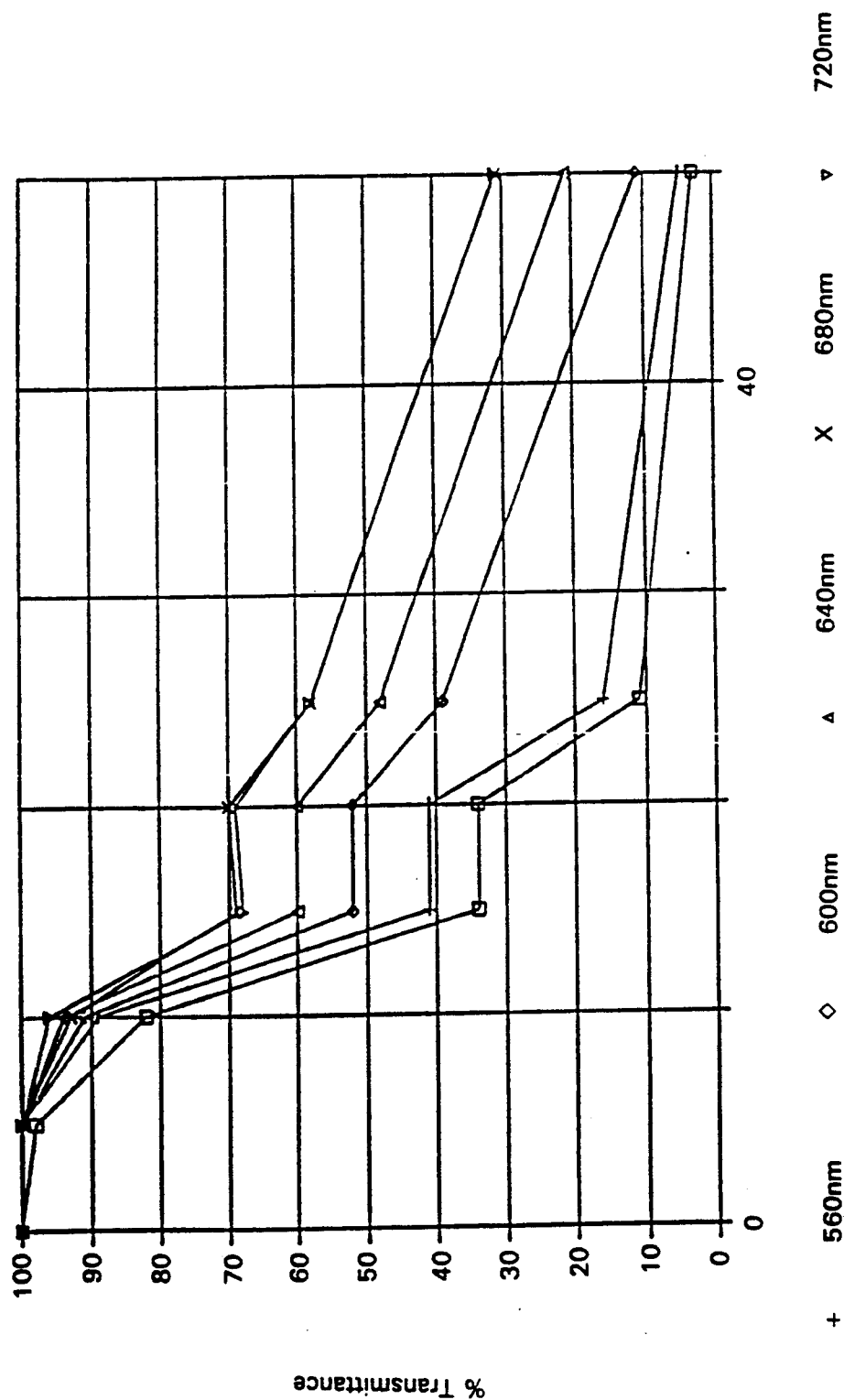
FIG. 9 shows the percent transmittance of varied wavelengths of light for varied dosages of an antifoulant solution including 40% polyisobutenylsuccinate in aromatic solvent for crude oil A 25%, 250 microliter stock.
Figure 10:
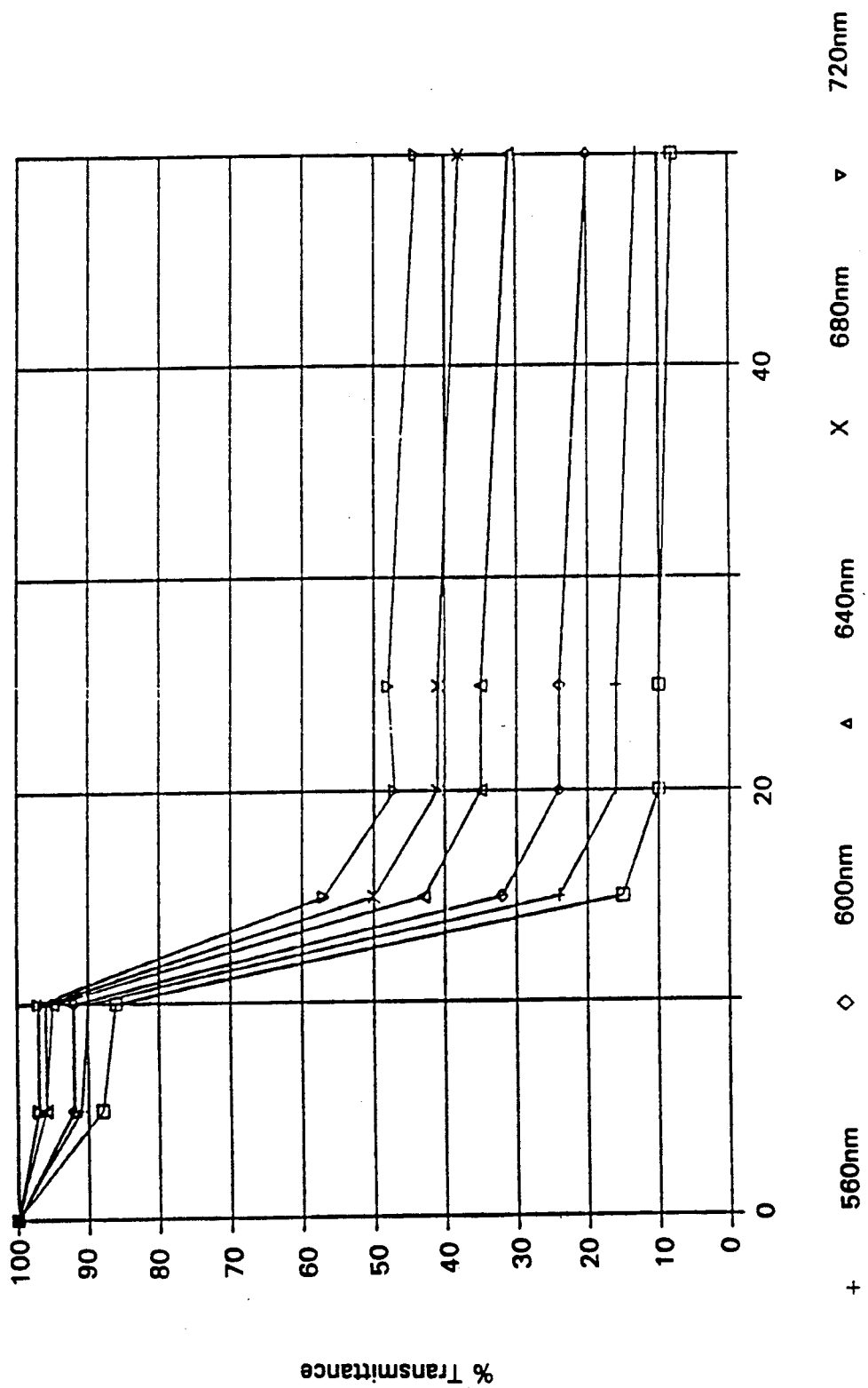
FIG. 10 shows the percent transmittance of varied wavelengths of light for varied dosages of an antifoulant solution including 40% polyisobutenylsuccinate in aromatic solvent for crude oil A 50%, 100 microliter stock.
Figure 13:
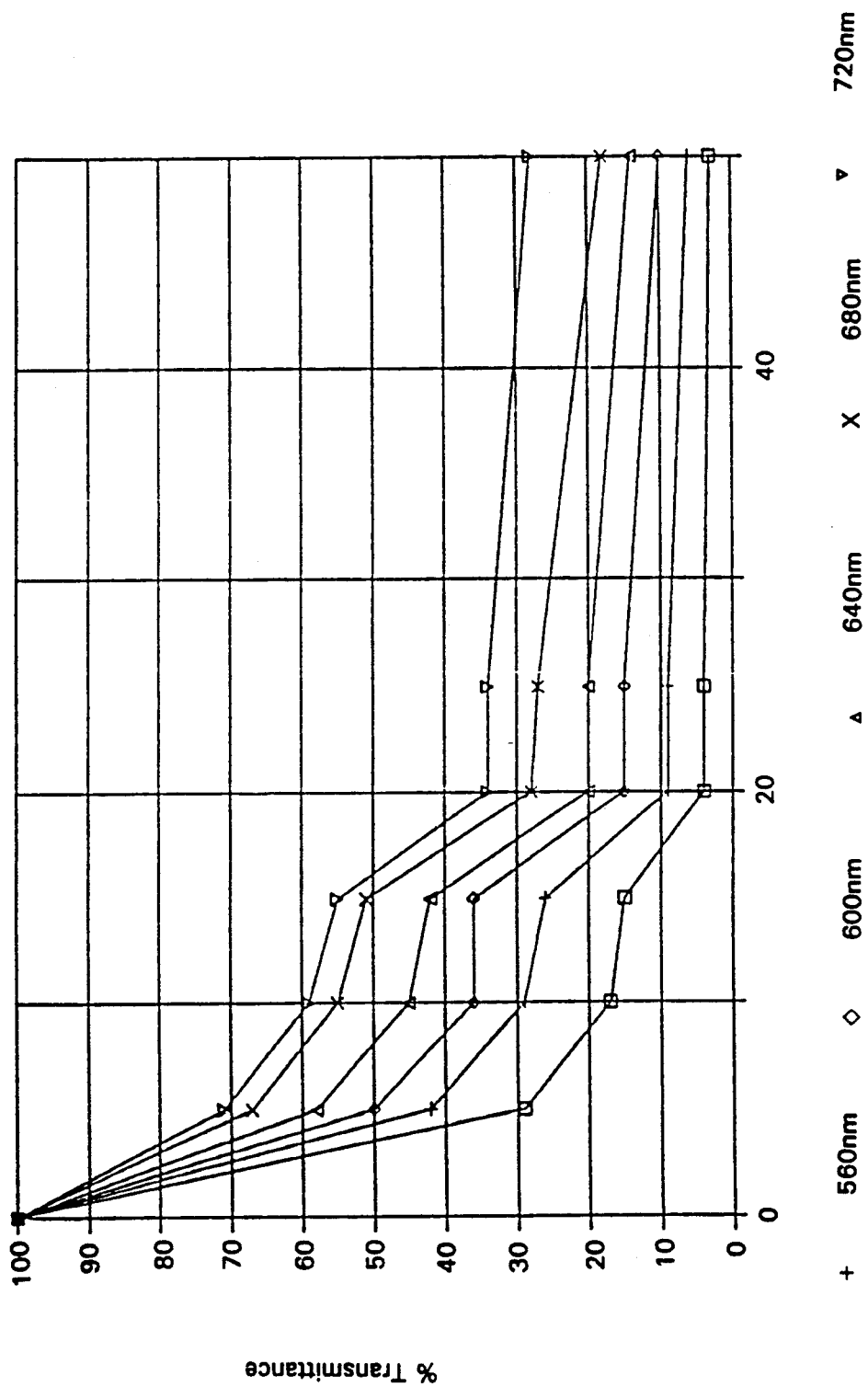
FIG. 13 shows the percent transmittance of varied wavelengths of light for varied dosages of an antifoulant solution including 40% polyisobutenylsuccinate in aromatic solvent for crude oil B 25%, 250 microliter stock.
Figure 14:
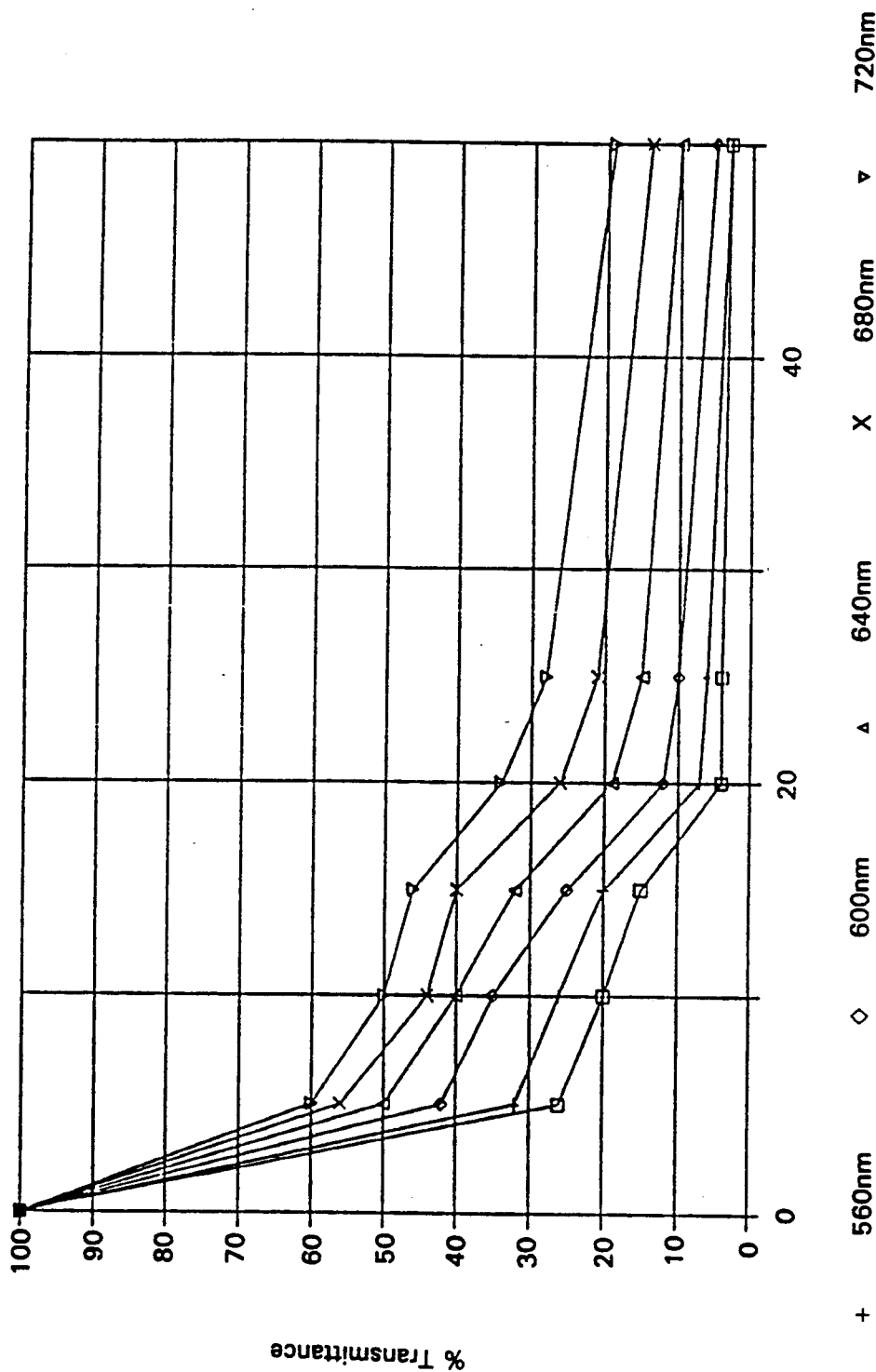
FIG. 14 shows the percent transmittance of varied wavelengths of light for varied dosages of an antifoulant solution including 40% polyisobutenylsuccinate in aromatic solvent for crude oil B 50%, 100 microliter stock.
Figure 17:
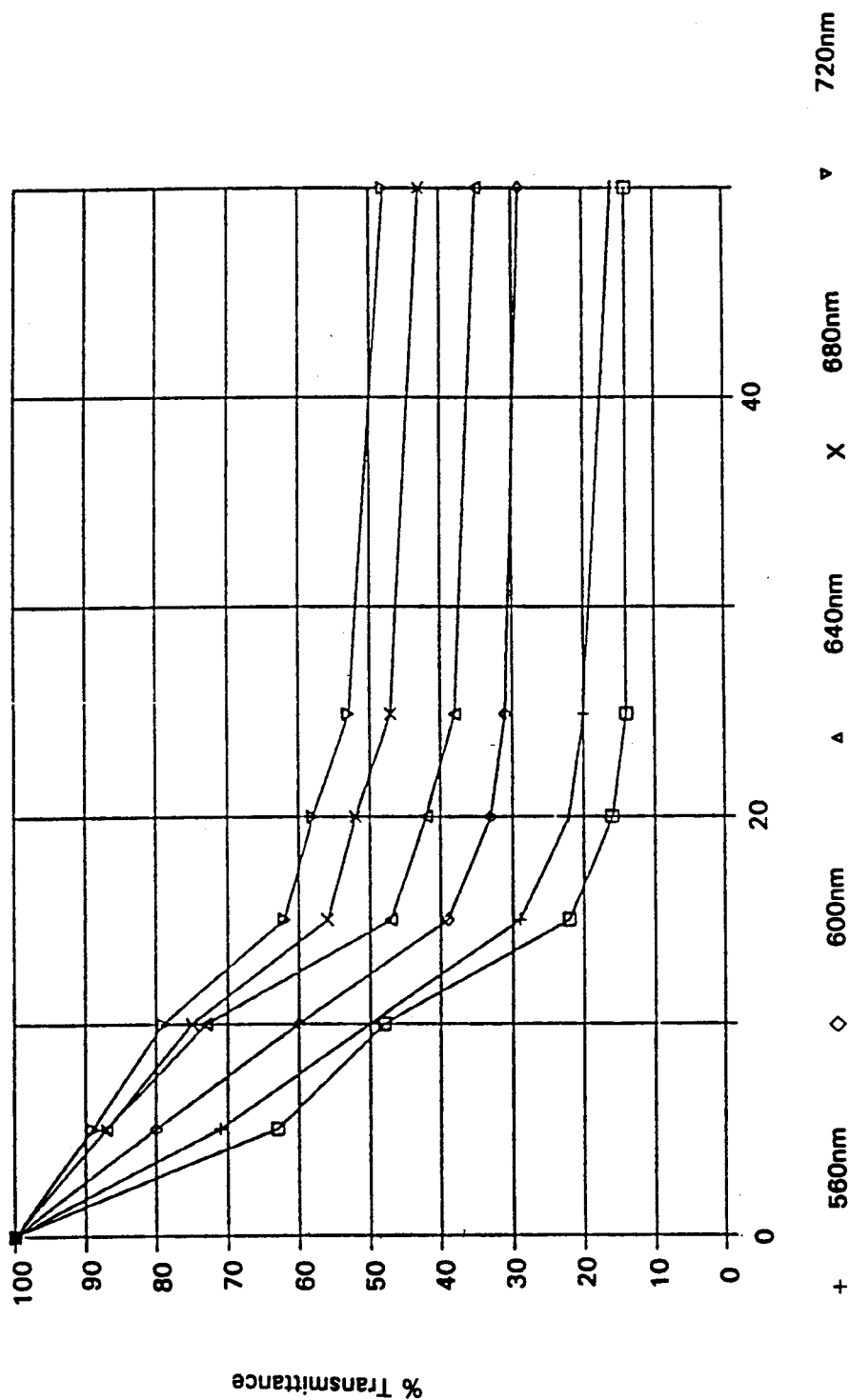
FIG. 17 shows the percent transmittance of varied wavelengths of light for varied dosages of an antifoulant solution including 40% polyisobutenylsuccinate in aromatic solvent for crude oil C 25%, 250 microliter stock.
Figure 18:
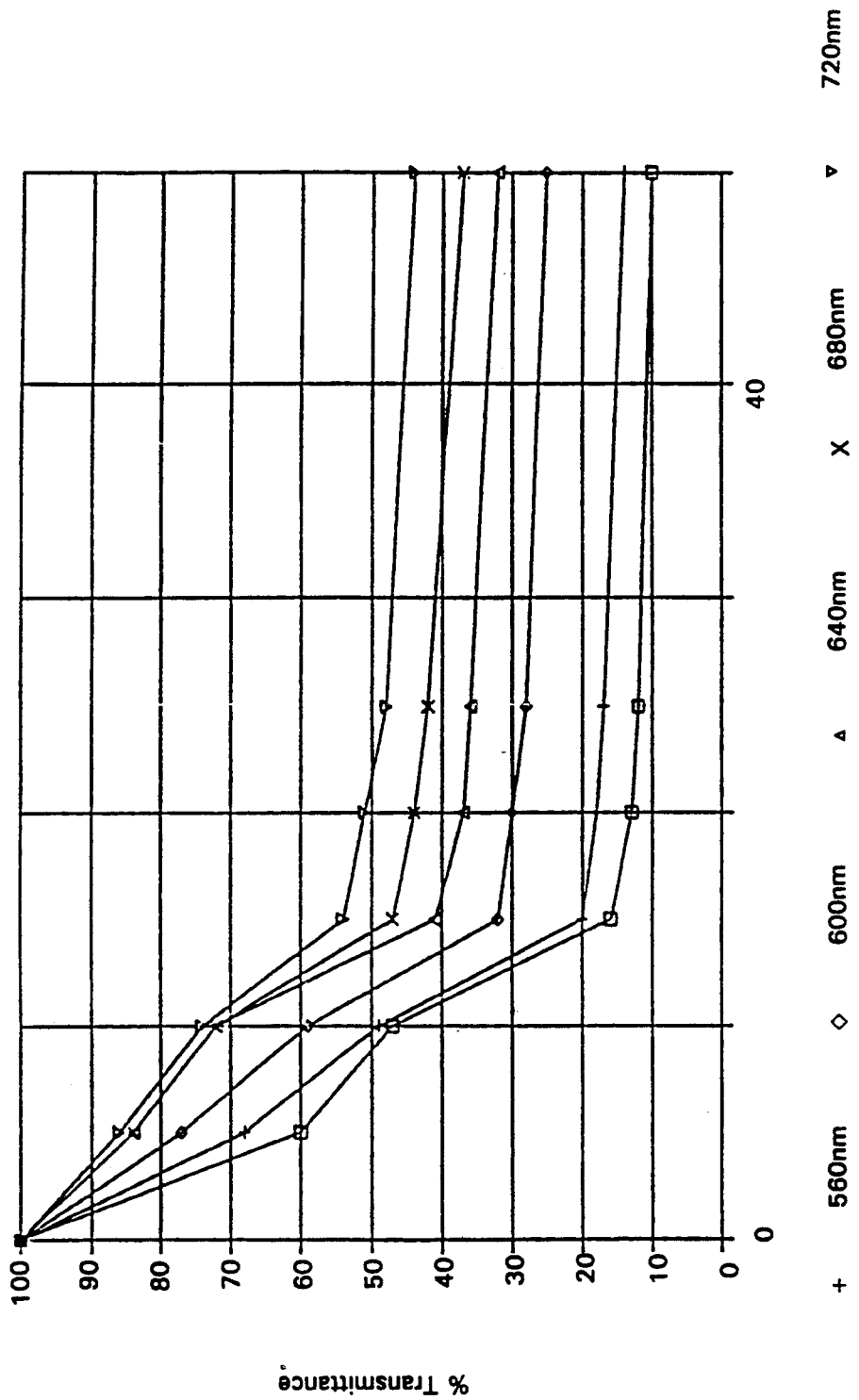
FIG. 18 shows the percent transmittance of varied wavelengths of light for varied dosages of an antifoulant solution including 40% polyisobutenylsuccinate in aromatic solvent for crude oil C 50%, 100 microliters stock.

Table II below includes a summary of the data obtained in Example 2. FIGS. 8–21 graphically represent the results of this testing.

TABLE II

| Crude Oil Name | *Amount Dosed | +Chemical Dosage | % T 520 nm | % T 560 nm | % T 600 nm | % T 640 nm | % T 680 nm | % T 720 nm |
|---|---|---|---|---|---|---|---|---|
| Crude Oil A 25% | 100 | 0 | 100 | 100 | 100 | 100 | 100 | 100 |
| | 100 | 5 | 63 | 70 | 77 | 81 | 87 | 77 |
| | 100 | 10 | 38 | 50 | 59 | 67 | 74 | 77 |
| | 100 | 15 | 33 | 43 | 52 | 62 | 70 | 75 |
| | 100 | 20 | 40 | 50 | 60 | 68 | 74 | 74 |
| | 100 | 25 | 38 | 49 | 59 | 68 | 72 | 75 |
| | 100 | 50 | 37 | 48 | 58 | 67 | 71 | 75 |
| Crude Oil A 25% | 250 | 0 | 100 | 100 | 100 | 100 | 100 | 100 |
| | 250 | 5 | 98 | 100 | 100 | 100 | 100 | 100 |
| | 250 | 10 | 82 | 89 | 91 | 94 | 93 | 96 |
| | 250 | 15 | 34 | 41 | 52 | 60 | 69 | 68 |
| | 250 | 20 | 34 | 41 | 52 | 60 | 70 | 69 |
| | 250 | 25 | 11 | 16 | 39 | 48 | 58 | 58 |
| | 250 | 50 | 3 | 5 | 11 | 21 | 31 | 31 |
| Crude Oil A 50% | 100 | 0 | 100 | 100 | 100 | 100 | 100 | 100 |
| | 100 | 5 | 88 | 91 | 92 | 96 | 96 | 97 |
| | 100 | 10 | 86 | 90 | 92 | 95 | 96 | 97 |
| | 100 | 15 | 15 | 24 | 32 | 43 | 50 | 57 |
| | 100 | 20 | 10 | 16 | 24 | 35 | 41 | 47 |
| | 100 | 25 | 10 | 16 | 24 | 35 | 41 | 48 |
| | 100 | 50 | 8 | 13 | 20 | 31 | 38 | 44 |
| Crude Oil A 50% | 200 | 0 | 100 | 100 | 100 | 100 | 100 | 100 |
| | 200 | 5 | 100 | 100 | 100 | 100 | 100 | 100 |
| | 200 | 10 | 99 | 97 | 98 | 98 | 99 | 99 |
| | 200 | 15 | 80 | 81 | 83 | 85 | 88 | 91 |
| | 200 | 20 | 63 | 69 | 72 | 74 | 79 | 88 |
| | 200 | 25 | 49 | 53 | 61 | 68 | 74 | 82 |
| | 200 | 50 | 20 | 26 | 28 | 36 | 45 | 55 |
| Crude Oil B 25% | 100 | 0 | 100 | 100 | 100 | 100 | 100 | 100 |
| | 100 | 5 | 21 | 29 | 38 | 46 | 56 | 63 |
| | 100 | 10 | 19 | 26 | 35 | 43 | 52 | 59 |
| | 100 | 15 | 11 | 17 | 25 | 33 | 43 | 51 |
| | 100 | 20 | 12 | 18 | 26 | 35 | 42 | 50 |
| | 100 | 25 | 12 | 17 | 26 | 34 | 42 | 51 |
| | 100 | 50 | 11 | 17 | 25 | 34 | 42 | 48 |
| Crude Oil B 25% | 250 | 0 | 100 | 100 | 100 | 100 | 100 | 100 |
| | 250 | 5 | 29 | 42 | 50 | 58 | 67 | 71 |
| | 250 | 10 | 17 | 29 | 36 | 45 | 55 | 59 |
| | 250 | 15 | 15 | 26 | 36 | 42 | 51 | 55 |
| | 250 | 20 | 4 | 9 | 15 | 20 | 28 | 34 |
| | 250 | 25 | 4 | 9 | 15 | 20 | 27 | 34 |
| | 250 | 50 | 3 | 6 | 10 | 14 | 18 | 28 |
| Crude Oil B 50% | 100 | 0 | 100 | 100 | 100 | 100 | 100 | 100 |
| | 100 | 5 | 26 | 32 | 42 | 50 | 56 | 60 |
| | 100 | 10 | 20 | 26 | 35 | 40 | 44 | 50 |
| | 100 | 15 | 15 | 20 | 25 | 32 | 40 | 46 |
| | 100 | 20 | 4 | 7 | 12 | 19 | 26 | 34 |
| | 100 | 25 | 4 | 6 | 10 | 15 | 21 | 28 |
| | 100 | 50 | 3 | 3 | 5 | 10 | 14 | 19 |
| Crude Oil B 50% | 200 | 0 | 100 | 100 | 100 | 100 | 100 | 100 |
| | 200 | 5 | 97 | 97 | 98 | 98 | 98 | 98 |
| | 200 | 10 | 89 | 89 | 90 | 91 | 92 | 93 |
| | 200 | 15 | 68 | 71 | 74 | 77 | 80 | 84 |
| | 200 | 20 | 58 | 63 | 68 | 72 | 76 | 78 |
| | 200 | 25 | 48 | 52 | 62 | 68 | 70 | 70 |
| | 200 | 50 | 16 | 23 | 29 | 35 | 40 | 45 |
| Crude Oil C 25% | 100 | 0 | 100 | 100 | 100 | 100 | 100 | 100 |
| | 100 | 5 | 75 | 79 | 82 | 85 | 89 | 90 |
| | 100 | 10 | 50 | 57 | 63 | 69 | 75 | 80 |
| | 100 | 15 | 32 | 45 | 50 | 61 | 67 | 73 |
| | 100 | 20 | 30 | 45 | 48 | 60 | 66 | 72 |
| | 100 | 25 | 28 | 42 | 45 | 57 | 64 | 70 |
| | 100 | 50 | 28 | 41 | 45 | 57 | 64 | 70 |
| Crude Oil C 25% | 250 | 0 | 100 | 100 | 100 | 100 | 100 | 100 |
| | 250 | 5 | 63 | 71 | 80 | 87 | 87 | 89 |

TABLE II-continued

| Crude Oil Name | *Amount Dosed | +Chemical Dosage | % T 520 nm | % T 560 nm | % T 600 nm | % T 640 nm | % T 680 nm | % T 720 nm |
|---|---|---|---|---|---|---|---|---|
| | 250 | 10 | 48 | 50 | 60 | 73 | 75 | 79 |
| | 250 | 15 | 22 | 29 | 39 | 47 | 56 | 62 |
| | 250 | 20 | 16 | 22 | 33 | 42 | 52 | 58 |
| | 250 | 25 | 14 | 20 | 31 | 38 | 47 | 53 |
| | 250 | 50 | 14 | 16 | 29 | 35 | 43 | 48 |
| Crude Oil C 50% | 100 | 0 | 100 | 100 | 100 | 100 | 100 | 100 |
| | 100 | 5 | 60 | 68 | 77 | 84 | 84 | 86 |
| | 100 | 10 | 47 | 49 | 59 | 72 | 72 | 74 |
| | 100 | 15 | 16 | 20 | 32 | 41 | 47 | 54 |
| | 100 | 20 | 13 | 18 | 30 | 37 | 44 | 51 |
| | 100 | 25 | 12 | 17 | 28 | 36 | 42 | 48 |
| | 100 | 50 | 10 | 14 | 25 | 32 | 37 | 44 |
| Crude Oil C 50% | 200 | 0 | 100 | 100 | 100 | 100 | 100 | 100 |
| | 200 | 5 | 84 | 86 | 89 | 92 | 94 | 95 |
| | 200 | 10 | 70 | 74 | 78 | 83 | 85 | 85 |
| | 200 | 15 | 58 | 62 | 69 | 72 | 74 | 75 |
| | 200 | 20 | 46 | 50 | 53 | 60 | 61 | 63 |
| | 200 | 25 | 32 | 36 | 43 | 49 | 51 | 53 |
| | 200 | 50 | 15 | 18 | 31 | 38 | 44 | 48 |
| Crude Oil B 75% | 50 | 0 | 100 | 100 | 100 | 100 | NA | NA |
| | 50 | 5 | 25 | 32 | 41 | 49 | NA | NA |
| | 50 | 10 | 16 | 21 | 27 | 33 | NA | NA |
| | 50 | 15 | 8 | 10 | 15 | 21 | NA | NA |
| | 50 | 20 | 8 | 10 | 15 | 21 | NA | NA |
| | 50 | 25 | 6 | 10 | 15 | 20 | NA | NA |
| | 50 | 50 | 5 | 9 | 12 | 18 | NA | NA |
| Crude Oil B 75% | 100 | 0 | 100 | 100 | 100 | 100 | 100 | 100 |
| | 100 | 5 | 70 | 73 | 77 | 82 | 89 | 94 |
| | 100 | 10 | 51 | 60 | 67 | 74 | 80 | 85 |
| | 100 | 15 | 36 | 43 | 51 | 57 | 65 | 70 |
| | 100 | 20 | 29 | 32 | 35 | 43 | 48 | 59 |
| | 100 | 25 | 20 | 24 | 31 | 36 | 41 | 47 |
| | 100 | 50 | 8 | 15 | 21 | 26 | 30 | 33 |

*Amount dosed in the amount of crude oil/toluene solution added in microliters.
+Chemical dosage is the concentration of an antifoulant solution including 40% polyisobutenylsuccinate in aromatic solvent added to the crude oil/toluene solution in units of ppm.
!% T 520 nm is the percent of light transmittance recorded by the photometer having a wavelength of 520 nm.

While the invention is susceptible to various modifications and alternative forms, specific embodiments thereof have been shown by way of example, in the drawings, and have been described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

I claim:

1. A process for optimizing the dosage of an asphaltene dispersant antifouling agent in a crude oil containing asphaltenes, the process including the steps of:
   a) mixing crude oil and an aromatic organic solvent in a volume ratio of from 1:3 to about 3:1 to form a mixture;
   b) subdividing said mixture into a plurality of vials;
   c) adding to each of the vials, a different dosage of the asphaltene dispersant antifouling agent;
   d) blending a quantity from each vial of step (c) with a quantity of at least one liquid paraffinic hydrocarbon, the volume blended from each vial of step (c) includes a sufficient volume of the crude oil such that the volume ratio of the crude oil to the liquid paraffinic hydrocarbon is from about 1:275 to about 1:125;
   e) maintaining each blend of step (d) in an undisturbed environment thereby allowing the nondispersed material in the blend to settle, thus leaving a supernate containing dispersed material;
   f) measuring the percent transmittance of light through a portion of the supernate from each blend of step (e); and
   g) comparing the percent transmittance of light through the super node of each sample to determine the optimum dosage of the antifouling agent in the crude oil, wherein said optimum dosage is the lowest dose necessary to disperse a sufficient quantity of asphaltene.

2. The process of claim 1 wherein the volume ratio of step (a) is further defined as about 1:1.

3. The process of claim 1 wherein the aromatic organic solvent is at least one aromatic organic solvent selected from the group consisting of benzene, alkylbenzenes, polynuclear aromatic compounds, and alkyl substituted polynuclear aromatic compounds.

4. The process of claim 1 wherein the aromatic organic solvent is at least one aromatic organic solvent selected from the group consisting of benzene, toluene, naphthalene, phenanthracene, and anthracene.

5. The process of claim 1 wherein the aromatic organic solvent is toluene.

6. The process of claim 1 wherein the asphaltene dispersant antifouling agent is a polymeric asphaltene dispersant.

7. The process of claim 1 wherein the dosage of the asphaltene dispersant antifouling agent added in step (c) is from agent 1 to about 100 ppm.

8. The process of claim 7 wherein the dosage of the asphaltene dispersant antifouling agent added in step (c) said second mixture is from about 5 to about 50 ppm.

9. The process of claim 1 wherein the liquid paraffinic hydrocarbon is an alkane having a straight carbon chain of from 5 to 17 carbon atoms in length.

10. The process of claim 9 wherein the liquid paraffinic hydrocarbon is further defined as having a carbon chain length of from 5 to 8 carbon atoms.

11. The process of claim 10 wherein said liquid paraffinic hydrocarbon is further defined a hexane.

12. The process of claim 1 wherein the volume ratio of step (d) is about 1:200.

13. The kit of claim 11 wherein the percent transmittance of light passed through a portion of the supernate is measured using a photometer.

14. The process of claim 13 wherein the percent transmittance of light passed through the supernate is measured in the wavelengths from about 520 to about 720 nm.

15. The process of claim 14 wherein the wavelength of light is further defined as about 640 nm.

16. A method for optimizing the dose of an asphaltene dispersant antifouling agent in a crude oil containing asphaltenes using the test kit of claim 34 which includes the steps of:
   a. diluting the crude oil with an equal amount of the aromatic organic solvent to form a first mixture;
   b. subdividing the first mixture into a plurality of vials;
   c. adding a different quantity of the solution comprising the asphaltene dispersant antifouling agent dissolved in an aromatic organic solvent to each of the vials of step (b);
   d. blending separately a portion from each of the vials of step (c) with a quantity of the liquid paraffinic hydrocarbon;
   e. maintaining each blend of step (d) in an undisturbed environment, thereby allowing the nondispersed material in the blend to settle, thus leaving a supernate containing dispersed material;
   f. measuring in a photometer the percent transmittance of light through a portion of the supernate of step (e); and
   g. comparing the recorded measurements of light transmittance through the supernate of step (e) for each sample to determine the optimal dose of the asphaltene dispersant antifouling agent in the crude oil, wherein the lowest dose necessary to disperse a sufficient amount of asphaltenes is the optimal dose of the asphaltene dispersant antifouling agent for the crude oil.

* * * * *

UNITED STATES PATENT AND TRADEMARK OFFICE
CERTIFICATE OF CORRECTION

PATENT NO. : 5,156,975
DATED : October 20, 1992
INVENTOR(S) : Mark A. Nelson

It is certified that error appears in the above-indentified patent and that said Letters Patent is hereby corrected as shown below:

On the title page, item [54] and column 1, line 4, "PROCESS" should be deleted.

At column 16, line 40, "super node" should read --supernate--.

At column 17, line 11, "kit" should read --process--.

At column 17, line 22, "using the test kit of claim 34" should be deleted.

Signed and Sealed this

Twelfth Day of October, 1993

Attest:

Attesting Officer

BRUCE LEHMAN

Commissioner of Patents and Trademarks